(12) United States Patent
Schloesser et al.

(10) Patent No.: US 12,178,611 B2
(45) Date of Patent: Dec. 31, 2024

(54) PERIPHERAL VENOUS CATHETER ASSEMBLIES WITH SENSORS AND RELATED METHODS

(71) Applicant: B.Braun Melsungen AG, Melsungen (DE)

(72) Inventors: Juergen Friedhelm Peter Schloesser, Neunkirchen am Brand (DE); Hang Khiang Chng, Singapore (SG); Aik Aun Tan, Penang (MY); Chee Mun Phang, Penang (MY); Jarryd Keng Gene Ng, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 897 days.

(21) Appl. No.: 17/056,369

(22) PCT Filed: May 27, 2019

(86) PCT No.: PCT/EP2019/063666
§ 371 (c)(1),
(2) Date: Nov. 17, 2020

(87) PCT Pub. No.: WO2019/228991
PCT Pub. Date: Dec. 5, 2019

(65) Prior Publication Data
US 2021/0244359 A1   Aug. 12, 2021

Related U.S. Application Data

(60) Provisional application No. 62/677,539, filed on May 29, 2018.

(51) Int. Cl.
*A61B 5/00* (2006.01)
*A61M 25/00* (2006.01)
*G16H 40/67* (2018.01)

(52) U.S. Cl.
CPC .......... *A61B 5/6852* (2013.01); *A61B 5/0022* (2013.01); *A61B 5/0084* (2013.01);
(Continued)

(58) Field of Classification Search
CPC ... A61B 5/6852; A61B 5/0022; A61B 5/0084; A61B 2017/00022; A61B 2017/00221;
(Continued)

(56) References Cited

U.S. PATENT DOCUMENTS

| 5,531,714 A | 7/1996 | Dahn et al. |
| 2002/0072680 A1* | 6/2002 | Schock ............ A61M 25/1006 606/192 |

(Continued)

FOREIGN PATENT DOCUMENTS

| CN | 108024729 A | 5/2018 |
| JP | 2007-530155 A | 11/2007 |

(Continued)

OTHER PUBLICATIONS

International Search Report and Written Opinion on corresponding PCT application (PCT/EP2019/063666) from International Searching Authority (EPO) dated Aug. 16, 2019.
(Continued)

*Primary Examiner* — Hien N Nguyen
(74) *Attorney, Agent, or Firm* — Alumen IP Law PC

(57) ABSTRACT

Catheters (104) with monitoring capabilities that can upload sensed or acquired data to a smart device (120) and/or a Cloud server (130). One or more sensors (106) can be located with a catheter assembly to collect data. The collected data can be processed by data analytics to analyze the data for usable information, such as to spot trends, patterns, and cause-effect relationships of the various detected conditions. The information can be viewed using an App or a web-browser dashboard or a local monitor.

19 Claims, 17 Drawing Sheets

(52) U.S. Cl.
CPC ......... *G16H 40/67* (2018.01); *A61M 25/0097* (2013.01); *A61M 2205/3306* (2013.01)

(58) Field of Classification Search
CPC .... A61B 5/0015; A61B 5/6876; G16H 40/67; G16H 50/20; G16H 40/63; G16H 20/17; G16H 20/40; A61M 25/0097; A61M 2205/3306; A61M 5/16831; A61M 25/0606; A61M 2005/16863; A61M 2205/3576
See application file for complete search history.

(56) References Cited

U.S. PATENT DOCUMENTS

| | | |
|---|---|---|
| 2007/0173735 A1 | 7/2007 | Callister et al. |
| 2009/0131777 A1 | 5/2009 | Simpson et al. |
| 2013/0165944 A1* | 6/2013 | Gal ..................... A61B 17/22 606/127 |
| 2015/0351645 A1* | 12/2015 | Hiltner ............... A61B 5/02156 600/486 |
| 2017/0086746 A1 | 3/2017 | Ofek et al. |
| 2019/0069812 A1 | 3/2019 | Isaacson et al. |
| 2020/0022637 A1* | 1/2020 | Kurzrock ........... G01N 21/4738 |

FOREIGN PATENT DOCUMENTS

| | | |
|---|---|---|
| WO | 2017/172388 A1 | 10/2017 |
| WO | 2018022916 A1 | 2/2018 |

OTHER PUBLICATIONS

Communication pursuant to Article 94(3) EPC for EP Application No. 19728359.1 (dated Feb. 29, 2024).

Wang et al, "Principles and Applications of Transducers," (Mar. 31, 2017).

First Office Action, KR Patent Application No. 10-2020-7037894, dated Jun. 27, 2024, pp. 1-10.

* cited by examiner

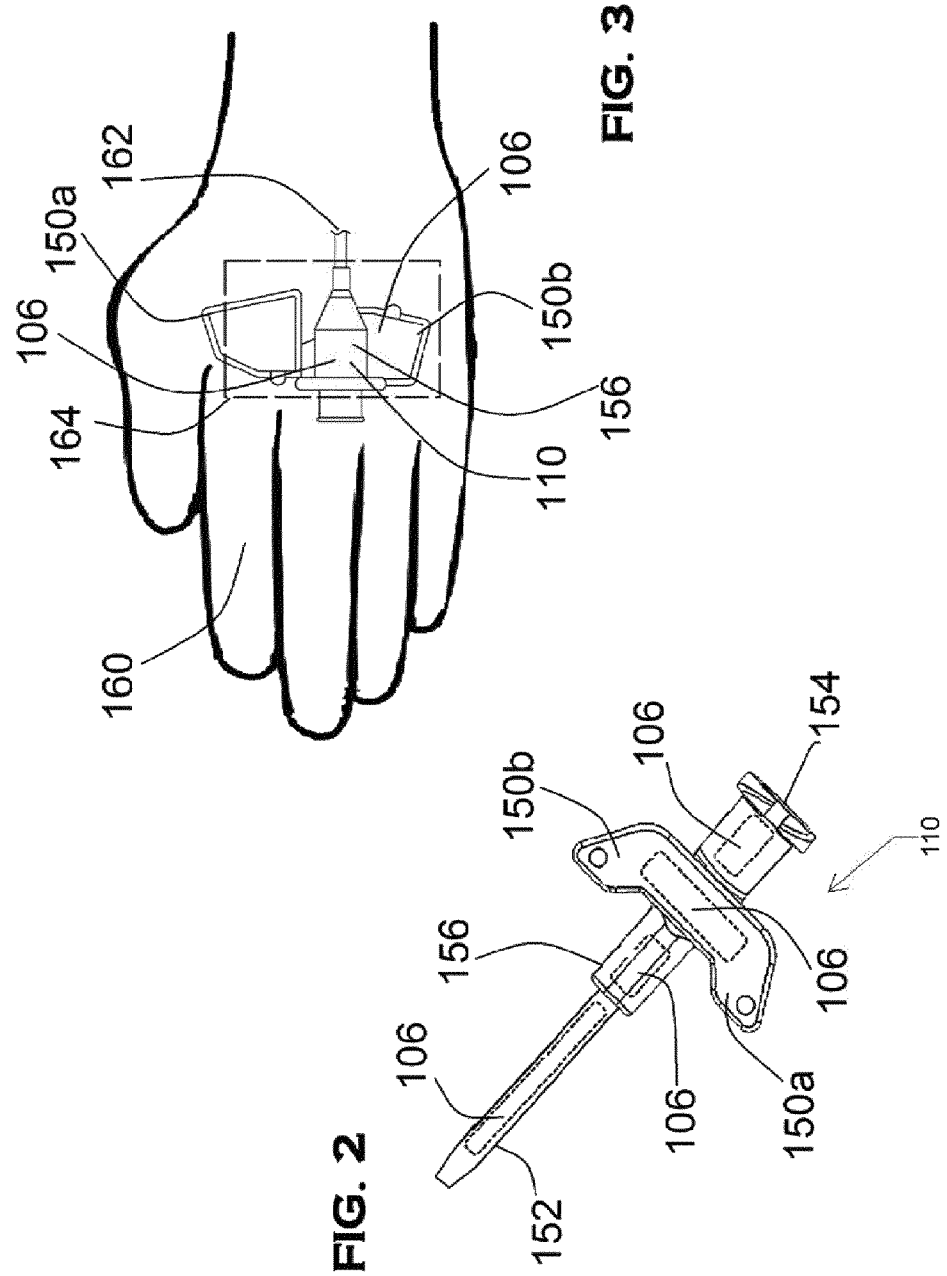

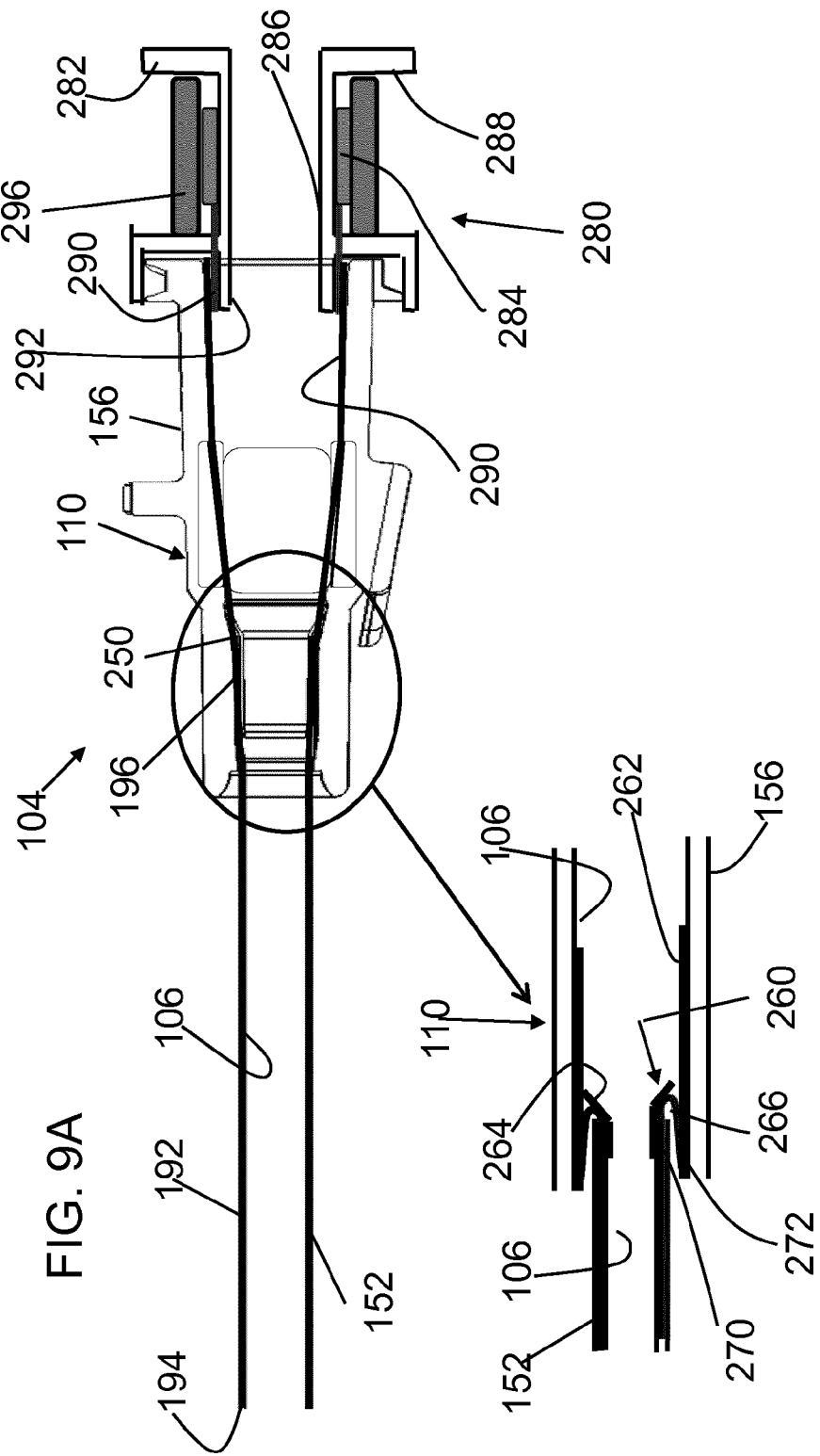

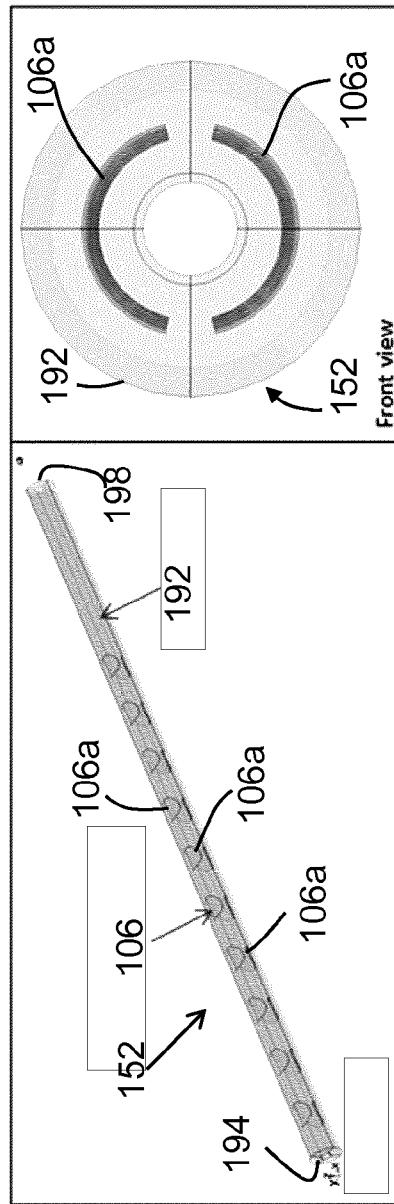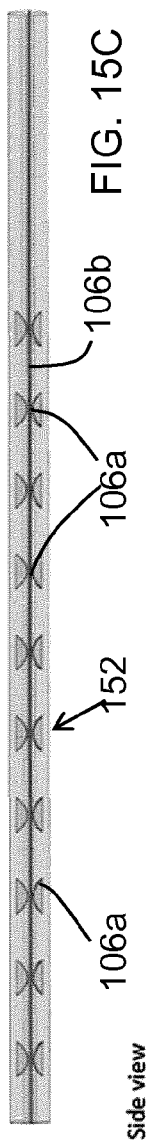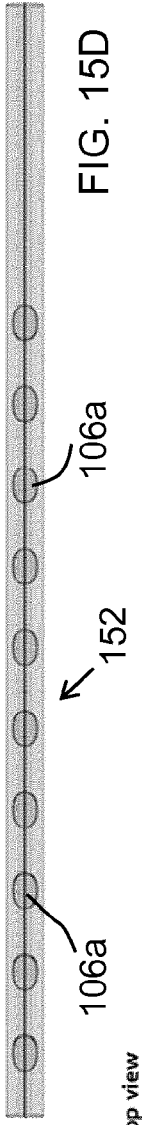

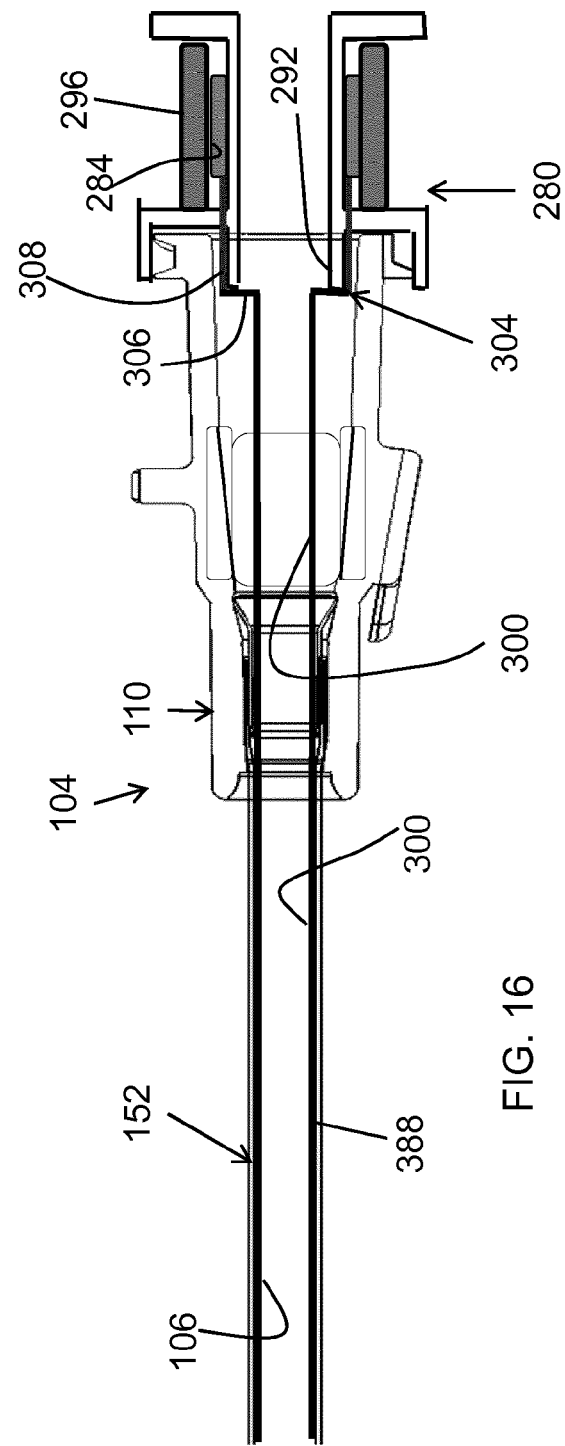

PERIPHERAL VENOUS CATHETER ASSEMBLIES WITH SENSORS AND RELATED METHODS

FIELD OF ART

The present invention is generally directed to catheter assemblies and more particularly to catheter assemblies, such as over-the-needle catheter devices, with sensors for status monitoring of human conditions and/or catheter conditions and related methods. Safety features, such as needle guards or needle shields, and flow control features, such as a septum, a valve, and a valve actuator for actuating the valve, can be incorporated with the catheter assemblies, such as with peripheral IVCs, central venous catheters, peripherally inserted central catheters and midline catheters.

BACKGROUND

Use of catheters, such as intravenous catheters, central venous catheters, peripherally inserted central catheters, and midline catheters, frequently requires a healthcare worker to carefully monitor environmental conditions of the patient and the catheter itself. However, medical procedures often require healthcare workers to multitask, increasing the chances of a mistake. Once a catheter assembly is connected to a patient and/or a fluid source (such as an IV fluid source), a practitioner's only visual indication of the status of the infusion fluid, the conditions of the catheter device, the position of the catheter hub, etc. is typically from visiting with the patient and observing the puncture site and the surroundings.

SUMMARY

The various embodiments of present catheter system have several features, no single one of which is solely responsible for their desirable attributes. Without limiting the scope of the present embodiments as set forth in the claims that follow, their more prominent features now will be discussed briefly.

Aspects of the present disclosure include a preferably intravenous catheter system comprising: a catheter hub comprising a hub body having an exterior and an interior; a catheter tube attached to the catheter hub; a sensor coupled to the hub body for sensing status of the catheter hub or for monitoring patient conditions; and at least one of a smart device and a Cloud server for collecting sensed data from the sensor.

The smart device is suitable for preferably wireless communication with the sensor of the preferably intravenous catheter system. The smart device can be an electronic device, generally connected to other devices or networks via different wireless protocols such as Bluetooth, NFC, Wi-Fi, 3G, etc., that can operate to some extent interactively and autonomously. The smart devices can be one of the following: smartphones, phablets and tablets, smartwatches, smart bands and smart key chains.

The sensor could be coupled to any part of the catheter to monitor a status. The sensor could be, for example, a first sensor coupled to interior of the hub body.

A second sensor can be included with the catheter system and wherein the second sensor can be coupled to the exterior or the hub body.

The second sensor can couple to a wing extending from the hub body. Additional or alternative sensors can be included with the catheter tube, such as forming part of the OD, ID, or interior of the catheter tube.

The one or more sensors can be used to measure and monitor any suitable metric, for example blood flow, pulse, blood pressure, blood oxygen levels, body temperature, localized skin temperature, pH value, occlusion of catheter, flow rate, etc.

Any suitable wireless transceiver, for example a BLE (Bluetooth Low Energy) module can electrically couple to the sensor for relaying sensed data to a smart device using a wireless connectivity.

Wireless transceivers could include, for example, a BLE transceiver, a Wi-Fi transceiver, an infra-red transceiver, and an RF (radio frequency) transceiver. Such transceivers could send and receive data, or could be a transmitter that only transmits data. A BLE module can electrically couple to the sensor and a gateway can comprise a BLE module and Wi-Fi module. In alternative embodiments, dedicated transmitter and receivers can be used instead of transceivers.

The sensed data can be collected by the Cloud server via the Wi-Fi module of the gateway.

The system can include a heat to electricity converter for powering the one or more sensors using ambient heat, such as heat from a patient.

The system can include a flexible supercapacitor for converting heat to electricity to power the one or more sensors.

The hub body of the catheter hub can comprise a first hub body section attached to a second hub body section. The two sections facilitate access to the interior of the hub body, before joining them together, for mounting or installing any number of components therein, such as sensors.

The sensor can comprise a plurality of discrete sensors distributed along a length of the catheter tube.

The preferably intravenous catheter system can further comprise a fiber optic sensor connecting the sensor and to an electronic connector assembly removably connected to the catheter hub.

The sensor mounted to the catheter tube can be a fiber optic sensor extending to an electronic connector assembly removably connected to the catheter hub.

A method for monitoring signals collected in a catheter assembly is disclosed. The method can comprise providing a sensor with a catheter hub having a hub body with an exterior and an interior; relaying data collected by the sensor wirelessly to at least one of a smart device and a Cloud server; and displaying information related to the data collected in a report.

Aspects of the invention include a method for manufacturing a catheter assembly with one or more sensors.

A further aspect of the invention is a method for manufacturing an peripheral intravenous catheter system described herein. Similar manufacturing concepts can be used for manufacturing central venous catheters, peripherally inserted central catheters, and midline catheters.

Aspects of the present invention further include a preferably intravenous catheter system comprising: a catheter hub comprising a hub body having an exterior and an interior; a catheter tube having a lumen attached to the catheter hub; a sensor mounted to at least one of the hub body and the catheter tube for sensing status of the catheter hub or for monitoring patient conditions; and at least one of a smart device and a Cloud server for collecting data sensed by the sensor.

The sensor can be a first sensor and can be mounted to the interior of the hub body.

The preferably intravenous catheter system can comprise a second sensor, and wherein the second sensor can be mounted to the exterior of the hub body.

The second sensor can be mounted to a wing extending from the hub body.

The second sensor can be mounted to the catheter tube.

The preferably intravenous catheter system can further comprise a BLE module electrically coupled to the sensor for relaying sensed data to a smart device using BLE connectivity.

The preferably intravenous catheter system can comprise a BLE module electrically coupled to the sensor and a gateway comprising a BLE module and Wi-Fi module.

The sensed data can be collected by the Cloud server through the Wi-Fi module of the gateway.

The hub body of a catheter hub can comprise a first hub body section attached to a second hub body section.

A needle guard for covering the needle tip can be included in the interior of the hub body. The needle guard can comprise a proximal wall with an opening and at least one resilient spring, such as a spring arm.

The hub body can comprise a side port and an open proximal end. A tubing can be connected to the side port and a fluid adaptor, such as a needleless valve can be connected at the end of the tubing, remote from the side port. The hub body can instead include a unitarily formed port, also known as a ported catheter.

A sleeve can be located in the hub body with a side port.

A valve and a valve opener can be located in the interior of the hub body.

The sensor mounted with the catheter tube can be lined to an interior of the catheter tube or embedded into a wall surface of the catheter tube.

A still further aspect of the present disclosure includes a preferably intravenous catheter system comprising: a catheter hub comprising a hub body having an exterior and an interior; a catheter tube having a lumen attached to the catheter hub; a sensor mounted to at least one of the hub body and the catheter tube for sensing status of the catheter hub or for monitoring patient conditions; and an electrical connector assembly comprising electronics for processing data sensed by the sensor, said electrical connector assembly comprising a connector housing attached to the hub body.

The electrical connector assembly can comprise an analog to digital converter and the connector housing can attach to a proximal end of the hub body.

The electrical connector assembly can comprise an analog to digital converter and the connector housing can attach to a side port of the hub body.

The electrical connector assembly can comprise a processor and a power source.

The connector housing of the electrical connector assembly is attachable and detachable from the hub body.

Another aspect of the present disclosure is a preferably intravenous catheter system comprising a catheter hub comprising a hub body having an exterior and an interior; a catheter tube having a lumen attached to the catheter hub; and a sensor mounted to at least one of the hub body and the catheter tube for sensing status of the catheter hub or for monitoring patient conditions.

The preferably intravenous catheter system can comprise at least one of a smart device and a cloud server for collecting sensed data.

A still further aspect of the present disclosure is a method for monitoring signals collected in a catheter assembly comprising: providing a sensor with a catheter hub having a hub body with an exterior and an interior; relaying data collected by the sensor wirelessly to at least one of a smart device and a Cloud server; and displaying information related to the data collected in a report.

The sensor of the catheter assembly can be in electrical communication with a lead on a computational core, which can be located external of a housing. The computational core can be a part of an electrical connector assembly, which can be threaded to a proximal end of the catheter hub. The catheter assembly can have a piston located inside a housing of the electrical connector assembly. A flow path of the catheter assembly can be defined at least in part between an exterior surface of the piston and an interior surface of the housing.

In some examples, a fiber optic sensor can be used as a sensing element, also known an intrinsic sensor, or as means for relaying signals from a remote sensor to the electronics that process the signals, also known as an extrinsic sensor. A fiber optic sensor can be used to measure strain, temperature, pressure and other quantities. Thus, aspects of the present disclosure is understood to include usage of a fiber optic sensor for intrinsic sensor purposes, for extrinsic sensor purposes, or for both purposes.

A system for administering therapeutic infusion treatment with monitoring capabilities in accordance with aspects of the present disclosure is disclosed. In an example, the system can monitor and record a patient's conditions when receiving the therapeutic infusion treatment and/or the status of the catheter assembly being used to administer the treatment.

By recording and monitoring various conditions and status of the patient and/or the catheter, vital clinical information can be provided to a clinician to alter or continue the course of treatment for optimum patient care. In some examples, the various conditions can be tracked and recorded in real-time to enable up to date feedback of the patient treatment progress. In exemplary embodiments, the catheter device can be other than a peripheral venous catheter, such as a central venous catheter, an intra venous catheter, a peripherally inserted central catheter ("PICC"), or a midline catheter. In accordance with aspects of the present system, a sensor equipped catheter assembly is provided with one or more sensors for monitoring patient conditions and/or catheter status.

As used herein, a "sensor" comprises a device that translates sensed data into an electronic signal that can be measured, such as a piezometer that translates sensed pressure data into a metric for measuring pressure, or a thermometer probe that translates measured current into a metric for measuring temperature. Sensors that are "mounted" to an element, such as an interior or exterior of a catheter hub or a needle hub, have an exposed input surface that shares an environment with the element. Sensors that are "embedded" within an element, such as within a wall of a needle or catheter tube, have an input surface that may not be exposed (e.g. a temperature sensor that senses ambient temperature through the wall surface) or may be exposed (e.g. a pH sensor having an input surface that is in fluid communication with an interior surface or an exterior surface of a catheter tube).

In an example, a assembly can have at least one sensor for sensing and/or monitoring patient conditions such as temperature or for sensing and/or monitoring the status of an interior or exterior environment of the catheter hub, such as for flow or pressure. The one or more sensors can comprise an accelerometer to detect movement, pressure sensor, temperature sensor, position and humidity sensors, to name a few non-limiting examples, and can be used to measure and monitor blood flow, pulse, blood pressure, blood oxygen levels, body temperature, localized skin temperature, pH value, occlusion of catheter, flow rate, etc.

Due to the size of typical catheter assemblies, the sensors are suitably sized and shaped accordingly and can be powered using body heat. For example, a heat to electricity converter can be used to charge a capacitor to then power a sensor for use with the devices of the present disclosure. Alternatively or additionally, a flexible supercapacitor can be used to power the sensors. Flexible supercapacitors have been discovered and described in US Publication No. 2014/0338715 and US Publication No. 2010/0051079 that can accumulate an electric charge using heat from the surroundings.

Power discharged from the flexible supercapacitor can be configured to power the one or more sensors and associated modules, such as a communications module for forwarding the detected signals to a server, controller or other modules for further processing. In some embodiments, the flexible supercapacitor could be used to charge a battery or a capacitor, which is, in turn, used to power one or more electronic devices, such as a sensor or a processor.

Flexible supercapacitors are known to researchers and scientists and have been experimented with in connection with wearable electronics. These thermally chargeable solid-state supercapacitor can be made from solid-state polymer electrolytes that produce large thermally induced voltage from a heat source, such temperature that emanates from a body. The voltage can then initiate an electrochemical reaction in electrolytes for charging. The capacitor can also use traditional electrical charging method for capacitors. The sensors can be integrated into wireless data transmission system for transmitting data to a local electronic device for use with an App or to a Cloud server via a Wi-Fi gateway for viewing, recording, trending, analyzing, etc., using a web-browser dashboard. In preferred embodiments, the flexible supercapacitor is coupled to an element of the catheter that is directly coupled to the patient, such as wings of the catheter hub, or to a portion of catheter tube.

The sensor equipped catheter assembly of the present invention can embody a catheter device as shown in U.S. Pat. Nos. 8,382,721; 8,540,728; and 8,597,249, the contents of which are expressly incorporated herein by reference. The catheter assembly can include one or more sensors located with the catheter hub, the needle hub, or both. The sensors can be located internally of the catheter hub and the needle hub and/or externally of the catheter hub and the needle hub depending on the conditions to be sensed and the type of data to be acquired.

In some examples, a needle guard can be provided with the catheter assembly and can be located outside of the catheter hub, such as in a third housing located between the catheter hub and the needle hub. In other examples, the needle can be covered after successful venipuncture using a spring-loaded needle hub with a depressible tab that pushes the needle hub and needle into a protective barrel or sheath.

The one or more sensors can be integrated with a Bluetooth Low Energy (BLE) module for communicating with a local smart device having Bluetooth connectivity to communicate data sensed or picked up by the one or more sensors to the local smart device. The local smart device can include a server, a laptop computer, a desktop computer, a handheld device, such as a smartphone or a tablet, or combinations thereof.

Custom program software can be provided with the local smart device to process and display the sensed data and to enable manipulation of the data for any number of views and reports, such as to spot trends, to track high or low set points, etc. As Bluetooth communication has a limited range, the local smart device is typically located within 15-20 meters from the catheter assembly to ensure strong wireless connectivity between the catheter assembly and the smart device.

Alternatively or additionally, the catheter assembly may communicate with a Cloud server via a gateway, which can be dedicated for the catheter system. In an example, the gateway may incorporate both a BLE module and a Wi-Fi module. Communication between the catheter assembly and the gateway can be via BLE connectivity and between the gateway and the Cloud server via Wi-Fi, such as using Wi-Fi to communicate to a router to then communicate to the Cloud.

Data sensed, collected, or picked up by the one or more sensors on the catheter assembly can therefore be transmitted to the Cloud server for recording, monitoring, analyzing and/or viewing via the gateway. In some examples, a BLE mesh network can be provided to extend the range between the catheter assembly and the gateway. In an example, the Cloud server is provided with data analytics and a web-browser dashboard to analyze uploaded data for usable information, such as to spot trends, patterns, and cause-effect relationships of the various detected conditions. Reports can be generated of the information uploaded and collected, such as provided in a bar chart form, in a line chart form, or in a text or written report form, or combinations thereof.

A clinician or an individual authorized by the patient, as provided by health and hospital policies, can view data stored on the Cloud server using a web-browser dashboard and a smart device from anywhere internet connectivity is available. Proper security and authentication may be required before the clinician and the authorized user can view the stored data.

In an example, a catheter hub has a pair of wings with a needle and a needle hub coupled to the catheter hub. The catheter hub has a catheter tube attached to the distal end of the hub body and has a proximal inlet or opening at an opposite end having a Luer taper for receiving a male Luer tip, such as a male infusion line, a syringe, or a male Luer adaptor. One or more sensors can be incorporated with the catheter assembly of the present embodiment, such as to the catheter tube, to the hub body of the catheter hub, to the wings, or combinations thereof. One or more sensors can be located interiorly of the hub body, interiorly of the catheter tube, externally of the hub body, externally of the wings, embedded in the wall of the hub body, or combinations thereof.

The catheter hub can be placed in fluid communication with a peripheral vein on a patient's hand at a puncture site. In some examples, rather than connecting to the peripheral vein at the hand, the puncture site can be at the forearm or elsewhere, such as near the chest for a central venous catheter or at the upper arm area for a PICC or midline catheter.

The catheter hub can be secured to the hand using a medical dressing, which can be secured to the hand via adhesive. Alternatively or additionally, the medical dressing can be incorporated with the wings without separately using adhesive, tape, or bandages to secure the catheter hub to the hand. One or more sensors of the present disclosure can be mounted to the exterior of the catheter hub, such as when mounting an accelerometer to the wings to detect movement of the catheter hub or the hand. In other examples, sensors can be mounted to the interior of the catheter hub, in the wall of the catheter hub, or in the lumen of the catheter tube to detect patient conditions, such as pH value, oxygen value, or local temperature.

In some examples, electronic components of the present system can be located both internally and externally of the catheter hub and the catheter tube. For example, the wireless module and the power module can both be located on the exterior of the catheter hub for powering the various sensors and modules and for sending collected signals to a local smart device or to the Cloud server. Sensors mounted in the interior of the hub body are thus in fluid communication with fluid passing through the catheter hub, including IV fluid and blood, while other modules, for example non-sensor modules, can be located externally and not be subjected to any wet or liquid environment.

One or more sensors can be coupled with the catheter hub to sense, detect, and/or monitor various conditions about the patient, such as body or local temperature, blood temperature, blood pH level, and/or about the status of the catheter hub, such as whether the hub body has moved (e.g. by triggering an alert when an accelerometer detects movement in a direction), whether a flow rate is detected through the catheter hub (e.g. by measuring flow rate or pressure), etc. Thus, the present catheter assembly, such as the catheter hub of the present catheter assembly, can be configured to not only serve as a vehicle for fluid infusion therapy but can also include one or more sensors to provide data on a number of different conditions that can be used by a clinician to gauge the effectiveness and various other aspects of the infusion therapy.

In an exemplary embodiment, a catheter hub has a hub body having a first hub section attached to a second hub section. The two hub body sections can provide convenient access to the interior of the hub body to facilitate mounting the one or more sensors and optionally other components, such as a valve and a valve opener, inside the hub body. After the one or more sensors, as well as after any valve, valve opener, and needle guard, where applicable, are mounted, the two hub body sections can be joined and secured to one another by adhesive, bonding, welding, or combinations thereof.

A catheter tube can attach to the distal end of the first hub section using conventional means, such as with a metal bushing. In some examples, the catheter hub can be an integrated infusion catheter having a side fluid port extending from the hub body with a tubing attached to the fluid port and a fluid adaptor attached at the opposite end of the tubing, such as a needleless connector. A septum can be located on the inside of the hub body of the integrated infusion catheter, proximal of the fluid port and distal of the proximal catheter hub opening. In alternative embodiments, the catheter hub can include a unitarily formed port, also referred to as a ported catheter, for receiving a male Luer tip directly, without the flexible tubing.

A needle hub having a needle with a needle tip and a change in profile, which can be a crimp, a bulge, a sleeve, or a material buildup, can be removed from a catheter hub, such as following successful venipuncture. The needle hub can have a needle hub body defining an interior flashback chamber with a proximal opening that typically has a vent plug (not shown) attached therewith to prevent blood flashback from leaking out the proximal opening. One or more sensors can be located with the needle hub, such as to the interior of the needle hub body to sense conditions of the blood, such as oxygen or pH levels.

A needle guard or tip protector can be moved to a distal end of the needle to surround or block the needle tip. Aspects of the needle guard are disclosed in U.S. Pat. Nos. 8,382,721; 8,540,728; and 8,597,249, previously incorporated by reference. In some examples, other needle safety devices or guards for preventing inadvertent needle sticks can be used with the catheter assembly with one or more sensors. For example, a spring loaded needle assembly can be activated to either push a shield over the needle in a protected position following use or the needle can be pushed into a stationary outer protective barrel for use to cover the used needle tip.

A catheter tube can be provided with a body with a distal opening, an enlarged proximal section having a proximal opening for receiving a metal bushing to secure the proximal section to the interior of the catheter hub. In an example, the interior of the tube body can be lined, partially or completely, with a polypyrrole sensing material. For example, the annular space of the catheter tube body can be lined with a polypyrrole sensing material for use to detect one or more of temperature, blood flow, blood pressure, blood oxygen levels, pH value, occlusion of catheter, etc. In an example, the sensing material inner layer can form a complete circumference interiorly of the outer catheter body material and can extend the length of the catheter tube or part of the length of the catheter tube.

The body of the catheter tube or the catheter hub can have one or more sensors impregnated or embedded into the wall layer thereof. The proximal section of the catheter tube can be made from a conducive metal material for acquiring signals from the sensing material and for connecting to other electronic modules, such as to a power source that utilizes heat to convert to electrical power and to a wireless signal transmitter. In some examples, the proximal section can be made from a conductive polymer material, also known as intrinsically conducting polymer or polymers (ICPs). ICPs are organic polymers that are known for conducting electricity.

In an example, the catheter system in accordance with aspects of the invention comprises a sensing module, a data processing module, and a communications module, which can be located on a catheter assembly or across several platforms, such as on a catheter assembly and in nearby peripheral equipment. A power module that uses heat to electricity conversion can be incorporated to energize the various sensors.

The sensing module can comprise one or more individual sensors for detecting any of the various parameters and conditions noted elsewhere herein. Individual sensors can be positioned inside the interior of the catheter body, the lumen of the catheter tube, and/or the interior of the needle hub. Individual sensors can also be mounted externally of the catheter hub body, such as on the wings of the catheter hub, on the hub body, and/or on the medical dressing. For example, an accelerometer may be mounted on the wings of the catheter hub to detect movement and a temperature sensor maybe used to detect surface skin temperature or local temperature of the patient.

A sensing module provided herein can include an analog to digital converter (A/D converter) for converting analog signals to digital signals. Optionally, the analog signals are simply communicated to a smart device or to the Cloud server, via a communications module, to be processed, converted, manipulated, etc. away or remote from the catheter assembly. For example, analog to digital conversion can be performed on the Cloud server. This allows the system of the present disclosure to operate on low power requirements and can be less costly to implement if the analog to digital converter can be processed elsewhere.

The present system can comprise a data processing module having a controller, which can comprise a microcontroller and/or a microprocessor, embodied in a printed circuit board (PCB). The data processing module can be provided with firmware and software to process the digital signals from the A/D converter to then perform one or more functions related to the processed signals, such as to send signals to a smart device, to the Cloud server via a gateway, etc.

Optionally, the data processing can be processed by the smart device or by the data analytics on the Cloud server. In preferred embodiments, the data processing module merely acts as a data queue that transmits sensor data to a transmitter, preferably a wireless transmitter such as wireless communications. Data processing module preferably has a transient or non-transient memory that saves data received from one or more sensors and transmits them to a remote computer system, such as cloud server or local smart device, which can process the data. In preferred embodiments, data processing module adds a unique label to each data segment that uniquely identifies a sensor, such as a temperature sensor within a catheter tube and a temperature sensor within a catheter hub, allowing the receiving computer system to categorize sensor data accordingly. Such labels could be added using any suitable means, such as an XML (extended meta-language) format. For example, each packet transmitted from a transceiver could comprise a time-stamp, a series of sensor metrics, a type of each sensor, and a unique identifier for each sensor. The unique identifier could be a location or a position within the catheter that allows a data processor system to calculate distance between at least two of the sensors.

The remote computer system could process the sensor data and perform any suitable analysis upon the data, such as compiling a data report or triggering an alert when a data threshold metric is passed, such as a blood temperature that has exceeded a threshold or fallen below a threshold, or a blood flow that has exceeded a threshold or fallen below a threshold. In some embodiments, the data processing module could be configured to perform such analysis, such as triggering an LED light on the catheter when a predetermined threshold is reached. In preferred embodiments, data from a plurality of sensors could be analyzed to create metrics, for example a data metrics from a first temperature sensor at a first location and a second temperature sensor at a second location could be utilized to calculate how the temperature differential between blood measured from the first temperature to the second location.

The present system can comprise a data communication module for communicating sensed signals to a smart device or to the Cloud server using any suitable wireless transceiver, such as BLE connectivity devices and Wi-Fi. Using data analytics, the signals can be displayed via charts, tables, and/or report format on the PC, laptop, mobile device.

Sensors discussed elsewhere herein can be made from materials that can include polypyrrole, carbon nanotubes, glass carbon, and polyacrylonoytile (PAN). The one or more sensors incorporated with the catheter assembly of the present embodiment, or to components thereof, can be connected, physically or wirelessly, to a wireless data transmitting component, such as to a BLE module, to transfer collected data to a smart device or a Cloud server for use by data analytics, an App, or a web-browser dashboard to analyze the uploaded data for usable information, such as to spot trends, patterns, and cause-effect relationships of the various detected conditions.

In some examples, a fiber optic sensor can be used as a sensing element, also known an intrinsic sensor, or as means for relaying signals from a remote sensor to the electronics that process the signals, also known as an extrinsic sensor. A fiber optic sensor can be used to measure strain, temperature, pressure and other quantities. Thus, aspects of the present disclosure is understood to include usage of a fiber optic sensor for both intrinsic sensor purposes, for extrinsic sensor purposes, or for both purposes.

For catheter assemblies with sensors and assembly components disclosed herein, it is understood that where a feature is shown but not expressly described and is otherwise the same or similar to the feature or features described elsewhere, the disclosed part or parts shown in all the drawing figures but not expressly described because of redundancy and because knowledge is built on a foundation laid by earlier disclosures may nonetheless be understood to be described or taught by the same or similar features expressly set forth in the text for the embodiments in which the feature or features are described. Said differently, subsequent disclosures of the present application are built upon the foundation of earlier disclosures unless the context indicates otherwise.

The disclosure is therefore understood to teach a person of ordinary skill in the art the disclosed embodiments and the features of the disclosed embodiments without having to repeat similar components and features in all embodiments since a skilled artisan would not disregard similar structural features having just read about them in several preceding paragraphs nor ignore knowledge gained from earlier descriptions set forth in the same specification. As such, the same or similar features shown in the following catheter assemblies incorporate the teachings of earlier embodiments unless the context indicates otherwise. Therefore, it is contemplated that later disclosed embodiments enjoy the benefit of earlier expressly described embodiments, such as features and structures of earlier described embodiments, unless the context indicates otherwise.

In an example, the needle can for use inside the catheter tube can instead be a stylet, or a solid needle shaft. In some examples, a guidewire is used with the catheter assembly to help guide placement of the catheter tube. The catheter hub has a catheter hub body and a catheter tube with a tube body attached to the hub body, such as with a metal bushing. In an example, the interior of the tube body can be lined, partially or completely, with a sensing material, such as a polypyrrole sensing material. For example, the annular space of the catheter tube body can be lined with a polypyrrole sensing material for use to detect one or more of temperature, blood flow, blood pressure, blood oxygen levels, pH value, occlusion of catheter, etc. In some examples, the sensor can be embedded inside the thickness of the catheter tube.

The catheter tube has a body with a distal opening and a proximal section made from a conducting material. In some embodiments, The body could comprise one or more sensors embedded within an insulating material electronically coupled to the conductive proximal section via an insulated path, such that conductive proximal section can abut an input port of an electronic device, such as an A/D converter or an input to a data processing module. Alternatively, the proximal section can be made from a polymer material and is lined with a sensing or conducting material, as further discussed below. The distal opening can have a reduced opening compared to other sections of the catheter tube to form a seal around the needle shaft or stylet. The proximal section of the catheter tube can be made from a conducive material for acquiring signals from the sensing material lining the interior of the tube body and for connecting to other electronic modules, such as to a power source that utilizes heat to convert to electrical power and to a wireless signal transmitter. Alternatively, the sensing material can extend past the proximal section 196 and an electrical connector is used to couple the sensor to other devices.

In some examples, the proximal section can be made from a conductive polymer material, also known as intrinsically conducting polymer or polymers (ICPs). ICPs are organic polymers that are known for conducting electricity. The sensor material can be made from materials that can include polypyrrole, carbon nanotubes, glass carbon, and polyacrylonoytile (PAN). In some examples, the sensing material at the tube body and the sensing material at the proximal section of the catheter tube can be integrally formed or can be singularly formed.

In an example, electrical communication between the sensor located with the catheter tube and the conductor located with the catheter hub can be provided through or by using an electrical connector. In an example, the electrical connector is made from a conductive polymer material, such as from ICPs, polypyrrole, carbon nanotubes, glass carbon, and polyacrylonoytile (PAN). In other examples, the electrical connector is made from a conductive metal material, such as from copper, brass, or their alloys. One or more optic fibers can alternatively be used for the sensor and/or the conductor, as previously discussed.

The connector can have a body portion and a flange portion having a gap therebetween. The body portion can contact or wedge against the sensor with the catheter hub. Part of the sensor with the catheter tube can be positioned in the gap. Once a metal bushing is pushed into the catheter hub to wedge the catheter tube between the catheter hub and the metal bushing, the flange can clamp against the proximal end of the catheter tube sensor of the catheter hub and the body portion of the electrical connector.

In an example, the catheter tube sensor has a proximal end that is longer than the proximal end of the catheter tube body so that a folded section of the catheter tube sensor is folded around the exterior of the catheter tube body to directly contact the body portion of the connector. This folded section allows the catheter tube sensor to directly contact the body section of the connector rather than only through the contact with the flange.

An electronic connector assembly can attach to the proximal end of the catheter hub body. The electronic connector assembly can comprise a connector housing and an electrical module. Said connector housing can attach to the proximal end of the catheter hub for mounting the electronics module for use with the sensor and the conductor.

In some examples, fiber optic sensors can be mounted with the catheter tube and coupled to the connector assembly. The connector housing can be made from a thermoplastic material and can have a male tip for inserting into the proximal opening of the catheter hub and a threaded collar for threaded engagement with external threads on the catheter hub. In other examples, the connector housing can be secured to the catheter 110 using different securing means, such as by adhesive, detents, bonding, welding or combinations thereof. The connector housing can be elongated and can have a Luer taper for receiving a male Luer tip and can include external threads for a threaded Luer connection.

A conductor can also extend externally of the body of the connector to present a surface for contacting the conductor mounted with the catheter hub. The male tip of the connector can be sized and shaped to wedge the two conductors into good solid contact and provide a seal at the interface thereof from fluid flow. The contact between the conductors at the interface of the catheter hub and the electronic connector assembly allows for electrical communication of the electrical module to the sensor of the catheter tube.

In an example, the electronic module can include a sensing interface, a communication interface, and a power source, as described elsewhere herein. A cover can be provided around the electric module to seal the module from damage or unwanted exposure. In an example, the cover can be a coat or layer of a silicone material or a sleeve.

In an example, a conductor contacts the sensor, directly or indirectly, inside the catheter tube. The conductor can be used as an extension or a coupling to couple the sensor inside the catheter tube to the electrical connector assembly, which comprises a connector or connector housing, an electrical module, and a cover. In an exemplary embodiment, the conductor is provided with a receiving end, which can be one of a receptacle or a plug. The tip of the connector can be provided with the other one of the receptacle or the plug. The receptacle connects to the plug to provide an electrical path between the conductor and the electrical module. Alternatively, a fiber optic sensor can be incorporated with the catheter tube and an optical transmission fiber is used to connect the sensor to the electrical connector assembly. In an example, the electrical assembly can be detachable from the catheter hub to disconnect the receptacle and the plug. The detachable configuration allows the electrical connector assembly to be detached from the catheter hub and re-used or re-purpose, such as with a different catheter assembly.

In an example, a connector housing of an electrical assembly is detachable from the proximal end of a catheter hub. The disconnection is possible by providing a connection between the sensor at the catheter tube and the conductor of the electrical assembly with a conductor of the catheter hub. A pressed fit or contact fit may be used to removably fix the connector to the catheter hub with threading via the threaded collar on the connector engaging the threads on the catheter hub.

In an exemplary embodiment, the hub body includes a side port having a channel or flow path in fluid communication with the interior cavity of the catheter hub. Although not shown, a valve in the form of a sleeve may be placed in the interior of the catheter hub to block the fluid path way at the intersection of the channel and the interior cavity. The sleeve prevents fluid from the interior cavity from leaking out through the side port. However, fluid pressure flowing through the side port, such as from a syringe or a drip line, can collapse at least part of the sleeve to allow fluid to flow into the channel to flow into the interior cavity and out through the catheter tube. A valve and a valve opener may be located in the proximal section of the interior cavity, as previously discussed with other catheter embodiments. In some examples, the sleeve and the valve can be a singularly or unitarily formed structure. The valve can be located proximally of the collapsible sleeve.

A sensor can be placed inside the catheter tube for connection with an electrical connector assembly via conductors located in the catheter hub body and in the side port. In an example, the sensor can be separately formed in the catheter tube then connected to the electrical connector assembly using an electrical conductor. In some examples, fiber optic as an extrinsic sensor can be used to relay signals. Alternatively, the connector can be formed continuously using a conductive polymer material, polypyrrole, carbon nanotubes, glass carbon, and polyacrylonoytile (PAN).

An electrical connector assembly can comprise a connector housing, an electrical module, and a cover attached to a side port. In an example, the electrical connector assembly is detachable from a side port and when disconnected can be refurbished or re-used with a different catheter hub. The disconnection can be made possible by providing a connection between the sensor and the conductor of the electrical assembly that is pressed fit or contact fit and held removably fixed by the connector engaging the side port of the catheter hub, such as by threading the threaded collar on the connector with the threads on the catheter hub.

Electronics of an electrical connector assembly can include an A/D converter for converting signals from the sensor or sensors mounted to the catheter hub and/or the catheter tube, as previously discussed. The A/D converter can be powered by a power source, which can be powered using body heat. For example, a heat to electricity converter can be used to charge a capacitor to then power the various components. Thermally chargeable solid-state supercapacitor can be made from solid-state polymer electrolyte that can produce large thermally induced voltage from a heat source, such as body temperature, to power the electronic components. In some examples, the heat to electricity converter can first charge a battery and the battery powers the electronic components.

The electrical connector assembly can further include a processor or CPU and a memory for storing and processing firmware and software. A pulse width modulator (PWM) for encoding the amplitude of a signal into a pulse width or duration of another signal for transmission and a universal asynchronous receiver-transmitter that acts as an interface to exchange data with a communications module and other serial devices can be incorporated to transmit and receive data. In other examples, a Bluetooth Low Energy (BLE) module may be incorporated to communicate using BLE signals to other BLE enabled devices, such as a smartphone, a laptop, or a tablet. In some examples, an integrated chip is incorporated with the electrical connector assembly, said integrated chip can include one or more modules, such as a communications module.

In an example, data transmitted by the electrical connector assembly can be communicated to a dedicated gateway having both a BLE module for receiving the data through Bluetooth communication from the electrical connector assembly and a Wi-Fi module for communicating the collected data to the Cloud, which can be understood to mean cloud computing where user access from anywhere is available via the internet. Once stored on the Cloud, users can access stored information using a computing device or a handheld device, such as a tablet or a smartphone, to view and analyze the collected data.

A local display unit can be provided for viewing, reading, and/or analyzing data collected from the electrical connector assembly. In an example, a portable viewing station comprising a maneuverable platform, such as a portable rollaway desk station, is provided with a monitor and a computing device, such as a computer or a laptop, programmed to view and process data received from the electrical connector assembly. In other examples, a tablet may be used by a practitioner to view and process data received from the electrical connector assembly. A computing device can include a wireless transmission reception module, a CPU, a memory, a display screen or area, and a power source to power the CPU and the display screen. In some examples, a dedicated hub with memory can be stationed with the electrical connector assembly to collect data. The dedicated hub can have connectivity, wired or wireless, to enable uploading of information contained therein to be accessed by a user, such as a doctor, nurse, or caregiver. A portable viewing station with a CPU and a monitor can be used to move from one patient room to another to access data from the dedicated hub for reviewing and analyzing patient conditions and/or equipment status.

In a further example, an IV catheter system comprising a catheter assembly and electronics for monitoring conditions of a patient and/or and the status of the peripheral venous catheter of the present invention. The electronic connector assembly can be without an integrated power supply. Instead, a removable power supply source or module for powering the electrical connector assembly can e provided. The removable power supply module can include a rechargeable battery having a light indicator for indicating the power level and firmware for controlling the power charging function. A pin connector can be provided to connect the power output of the battery to the electrical connector assembly.

Another alternative embodiment of a catheter tube can have a body with a distal opening, and a proximal opening for receiving a metal bushing to secure the proximal section to the interior of a catheter hub, such as one of the catheter hubs described elsewhere herein. In an example, the interior of the tube body can be lined, partially or completely, with a polypyrrole sensing material inside a conventional catheter tube, such as one made from a polyurethane (PU) material. For example, the annular space of the catheter tube body can be lined with a polypyrrole sensing material for use to detect one or more of temperature, blood flow, blood pressure, blood oxygen levels, pH value, occlusion of catheter, etc. In the present embodiment, the sensing material comprises a plurality of spaced apart or discrete sensors distributed along a length of the catheter tube, preferably embedded within a wall of the catheter tube. For example, the discrete sensors can each embody a ring shape, a round shape, an oval shape, or polygonal shape polypyrrole sensing material to enable sensing at discrete points along the catheter tube. The plurality of discrete sensors can also embody a web of polypyrrole sensing material for sensing at discrete points along the catheter tube. The discrete sensors can join discrete conductive traces or conductors or can be interconnected through other sensing materials.

As used herein, sensors that are discrete from one another have separate electronic output paths that couple to a data processing module in parallel, such that data from one sensor does not corrupt data from another sensor. This allows each sensor to collect data discretely from other sensors, even if individual sensors are fungible, allowing a data processing module or computer system to compare data between multiple sensors within the same catheter system. In some embodiments, a catheter tube may comprise a plurality of discrete sensors of different types as well as different outputs. For example, the discrete sensors could comprise both temperature sensors and pH sensors, and/or even pressure sensors. In some embodiments, sensors of different types could be grouped, for example in a first third of catheter tube, the sensors could be temperature sensors, in a second third the sensors could be pH sensors, and in a last third the sensors could be pressure sensors. The outputs of all of the sensors in a single catheter tube preferably lead to a common bus, such as an A/D converter bus, or a processor bus, allowing a processor to organize the data into a queue for transport via a transceiver.

In another example, the catheter tube can have one or more discrete sensors impregnated or embedded into the wall layer thereof. The proximal section of the catheter tube can be made from a conducive metal material for acquiring signals from the discrete sensors and for connecting to other electronic modules, such as to a power source that utilizes heat to convert to electrical power and to a wireless signal transmitter. In some examples, the proximal section can be made from a conductive polymer material, also known as intrinsically conducting polymer or polymers (ICPs). ICPs are organic polymers that are known for conducting electricity. In yet other examples, optic fiber sensors can be used to transmit information from the discrete sensors to an electrical connector assembly, as described elsewhere herein.

The discrete sensors can be distributed along the length of the catheter tube. In some examples, the discrete sensors can extend between 10% to 100% of the length of the catheter tube, with 20% to 90% being more preferred. The discrete sensors can be evenly spaced along a length of the catheter tube or randomly spaced along the length of the catheter tube. Here, each sensor has two discrete sensor inputs, one on a top side of catheter tube and another on a bottom side of catheter tube, both of which lead to an output bus. Wire can be a bus that transmits each sensor output discretely. In some embodiments, each set of up/down sensors could be coupled to a common bus terminals, and in other embodiments each set of up/down sensors are coupled to discrete bus terminals, allowing a data processor to compare sensor data between a sensor on a top side of catheter tube and a bottom side of catheter tube.

By coupling data sensors to a bus, this allows a data processor to compare sensor data with one another, such as a temperature at one point of the catheter tube against a temperature at another point of the catheter tube. This is particularly useful in embodiments having catheter tubes longer than a few inches, such as a one-foot catheter tube or a two-foot catheter tube. Data processing modules receiving sensor data could then glean additional data metrics via comparative analysis between received sensor data, such as pH or temperature differentials between different points along a length of a catheter tube.

Another alternative catheter assembly comprises a conductor contacts a sensor, directly or indirectly, inside the catheter tube. The conductor can be used as an extension or a coupling to couple the sensor inside the catheter tube to the electrical connector assembly, which comprises a connector, an electrical module, and a cover. In an embodiment, the conductor is provided with a receiving end, which can be one of a receptacle or a plug and a distal end that extends into the catheter tube to couple to the sensor at a location inside the catheter tube. The tip of the connector can be provided with the other one of the receptacle or the plug. The receptacle connects to the plug to provide an electrical path between the conductor and the electrical module. In an example, the conductor can instead be a fiber optic sensor for transmitting signals form the sensor to the electrical connector assembly.

A sensor equipped catheter assembly can comprise a catheter hub comprising a hub body having a pair of wings and a catheter tube attached at a distal end of the hub body and extending in a distal direction, terminating with a tapered distal opening. The hub body has a first hub section and a second hub section, which may be referred to as a distal hub section and a proximal hub section, respectively.

An electrical connector assembly is threadedly connected to the proximal hub section or second hub section of the catheter hub. The electrical connector assembly comprises a connector housing having a distal end and a proximal end. In an example, the distal end comprises a collar for receiving a sensor module, which has a collar for threading to the external threads on the proximal hub section. The connector housing comprises an elongated open end at the proximal end for receiving a male Luer tip, such as an IV connector or a syringe tip. In an example, the elongated open end can be a threaded female Luer. The electrical connector assembly can be separated from the catheter hub by un-threading the collar from the second hub section of the catheter hub.

The connector housing of the electrical connector assembly can have an inlet, a threaded female Luer at the inlet, and a collar at an opposite end. In an example, the collar is a slip-on collar for receiving the sensor module without threading. The connector housing has a body with a wall structure made from a thermoplastic material defining an internal bore that is sized and shaped to receive an elastic piston and a shoulder located between the inlet and the body.

The piston, which can fit within the bore of the housing, may be made from a silicone material and provided with a head section, a neck section, a shoulder, a body section, and an enlarged base, which can resemble a flange. The body section and optionally the shoulder can be hollow so that when the piston is located inside the housing and is pushed by a male tip inserted into the open proximal end of the housing, the piston collapses against the restrain of the sensor module. When the male tip is removed from the open proximal end, the piston can expand or return to its less compressed state so that the head of the piston expands into the inside bore at the inlet section to block the inlet opening from fluid flow thereacross.

In an example, the combination housing, piston, and end fitting on the sensor module resembles a female needleless connector. In a particular example, the combination housing, piston, and end fitting on the sensor module resembles female needleless connectors disclosed in U.S. Pat. No. 7,591,449, which discloses a piston located inside a housing and wherein the piston comprises a Y-slit, among other embodiments. The combination housing, piston, and end fitting on the sensor module can also resemble female needleless connectors disclosed in U.S. Pat. No. 9,695,953, which discloses a piston located inside a housing and wherein the piston comprises a spiral cut, among other embodiments. The contents of U.S. Pat. Nos. 7,591,449 and 9,695,953 are expressly incorporated herein by reference.

The sensor module can comprise a central conduit having a bore for fluid flow and a plurality of sensors, which can be the same as other sensors described elsewhere herein. The central conduit can extend from a male Luer to form a Luer fit with the inlet of the proximal hub section of the catheter hub. A threaded collar surrounds the male Luer and is sized and shaped to threadedly engage the external threads of the proximal hub section of the catheter hub.

A base drum is connected to the collar and has an outside diameter that is smaller than that of the collar for insertion into the collar of the housing. A shoulder between the base drum and the collar of the sensor module is configured to press or abut against the end edge of the collar of the housing. A plurality of electrical leads are electrically coupled to the plurality of sensors, such as by co-molding or insert molding, and are each provided with a radial section and an axial section. The radial section of each lead allows the lead to extend radially and then axially along the lengthwise direction of the housing to then contact the corresponding lead on the computational core.

A head drum extends from the base drum, which has a landing and a projection. The projection is sized and shaped to project into the open end of the piston at the base and the flange on the base is configured to press against the landing.

A plurality of flow passages are provided through the head drum and in fluid communication with the bore of the central conduit and the male Luer. Thus, when the piston is activated, a flow path is provided between the inlet at the head and the annular space between the exterior surface of the piston and the interior surface of the housing. The flow path is in fluid communication with the plurality of flow passages at the head drum, and the bore of the central conduit and the male Luer. The housing and the sensor module may be more permanently secured to one another by bonding, welding, or both.

The computational core may be mounted around the outside of the housing at the body section. In an example, the computational core comprises a body having a hollow center for placement over or around the housing. The body of the computational core may be made from a dielectric material and provided with traces or leads for connection to the leads on the sensor module and to circuitries and a power supply mounted to the body. The power supply can comprise a rechargeable battery. In an example, the circuitries can comprise components discussed elsewhere herein for use to relay or process sensed data from the sensors located on the sensor module to a remote server or processor. In an example, the computational core is separable from the leads of the sensor module and from the housing. For example, the computational core can be separated for re-use after disposal of the catheter hub.

A protective cover can be provided to cover the computational core, the various leads, and the various circuitries from potential damage and/or shorting. The protective cover can be made from a non-conducting or dielectric material and placed over both the computational core and the housing. In an example, the protective cover can be made from a silicone material or silicone rubber and can be provided with enlarged pockets and contoured surfaces for placement over the computational core and the housing and not interfere with electrical signals and connections. Such enlarged pockets and contoured surfaces could allow for the body to be placed within protective cover in a self-orienting manner. The protective cover has an open end for sliding over the computational core and the housing and can be made sufficiently flexible to facilitate mounting.

In use and similar to the needleless connectors disclosed in the '449 and 953 patents, when a male medical implement, such as a syringe tip or an IV connector, is connected to the inlet of the housing, the piston is compressed and a fluid path way is opened between the exterior surface of the piston and the interior surface of the housing. The fluid pathway is also in fluid communication with the flow passages at the head drum and the bore of the central conduit of the sensor module. When the piston is compressed as described, fluid can flow into the catheter hub and the catheter tube from the proximal end of the housing, such as during IV fluid administration, or fluid can be aspirated out of the proximal end, such as into a barrel of a syringe.

When the male medical implement is removed from the inlet of the housing, the piston is allowed to expand and the head is returned to the inside area of the inlet of the housing to close off the inlet from further fluid flow. Following treatment or whenever the catheter hub is replaced for a new catheter, the electrical connector assembly can be removed and re-used.

Such computing assemblies that allow a computational core to electronically engage with one or more conductive outputs from sensors within central conduit via a screw-on connection could be used to efficiently connect computational apparatuses to a catheter having a plurality of sensors.

In some embodiments, a computational core could be coupled to a single catheter hub, for example an intravenous catheter hub, a midline catheter hub, or some peripherally inserted central catheters, such as those disclosed in U.S. Pat. No. 6,544,251. In catheters that have a plurality of hubs, for example a central venous catheter such as those disclosed in U.S. Pat. No. 9,504,806 or 6,723,084, each catheter hub could comprise a discrete computational core configured to wirelessly transmit sensor data to a common computer system. Catheters having a plurality of hubs that have minor branches that lead to a common main catheter branch preferably have one catheter hub having a conductive bus that couples to sensors embedded in both the main branch and minor branch of the catheter, while all other catheter hubs have a conductive bus coupled only to sensors in the associated minor branch of the catheter hub.

Methods of making and of using the sensor equipped catheter assemblies described herein and their components are within the scope of the present invention.

BRIEF DESCRIPTION OF THE DRAWINGS

These and other features and advantages of the present devices, systems, and methods will become appreciated as the same becomes better understood with reference to the specification, claims and appended drawings wherein:

FIG. 2 is a bottom plan view of a catheter assembly shown without the needle and needle hub and with one or more sensors.

FIG. 3 shows a catheter hub having a catheter tube penetrating a puncture site on a hand to gain access to the peripheral vein.

FIG. 9A is a schematic depiction of a catheter assembly comprising a sensor and an electrical connector assembly for collecting and transmitting data and FIG. 9B is an enlarged view of an electrical connector.

FIGS. 15A-15D show different views of a catheter tube having discrete sensors distributed along a length of the catheter tube.

FIG. 16 a schematic depiction of a catheter assembly comprising a sensor and an electrical connector assembly for collecting and transmitting data.

DETAILED DESCRIPTION

The detailed description set forth below in connection with the appended drawings is intended as a description of the presently preferred embodiments of catheter devices or assemblies (e.g. central venous catheters, intra venous catheters, peripherally inserted central catheters, and midline catheters) with monitoring capabilities provided in accordance with aspects of the present devices, systems, and methods and is not intended to represent the only forms in which the present devices, systems, and methods may be constructed or utilized. These catheter devices are also known or referred to as over-the-needle catheter devices. Unless the context indicates otherwise, the different types of over-the-needle catheter devices can generally be referred to as catheter devices or assemblies. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
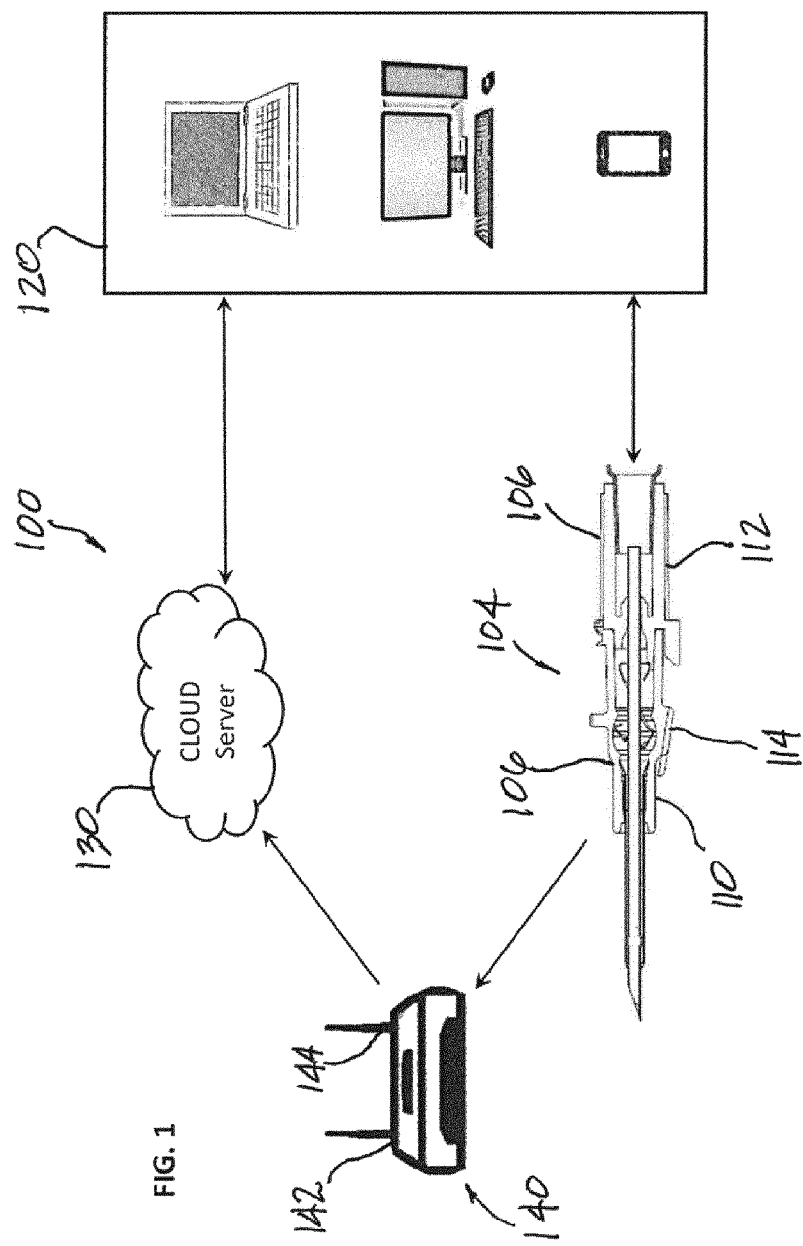
FIG. 1 is schematic system diagram depicting an intravenous catheter assembly for administering therapeutic infusion treatment with monitoring capabilities.

FIG. 1 depicts a system 100 for administering therapeutic infusion treatment with monitoring capabilities in accordance with aspects of the present disclosure. In an example, the system 100 can monitor and record a patient's conditions when receiving the therapeutic infusion treatment and/or the status of the peripheral venous catheter being used to administer the treatment. By recording and monitoring various conditions and status of the patient and/or the catheter, vital clinical information can be provided to a clinician to alter or continue the course of treatment for optimum patient care. In some examples, the various conditions can be tracked and recorded in real-time to enable up to date feedback of the patient treatment progress. In exemplary embodiments, the catheter device can be other than a peripheral venous catheter, such as a central venous catheter, an intra venous catheter, a peripherally inserted central catheter ("PICC"), or a midline catheter. In accordance with aspects of the present system 100, a sensor equipped catheter assembly 104 is provided with one or more sensors for monitoring patient conditions and/or peripheral venous catheter status. As used herein, a "sensor" comprises a device that translates sensed data into an electronic signal that can be measured, such as a piezometer that translates sensed pressure data into a metric for measuring pressure, or a thermometer probe that translates measured current into a metric for measuring temperature. Sensors that are "mounted" to an element, such as an interior or exterior of a catheter hub or a needle hub, have an exposed input surface that shares an environment with the element. Sensors that are "embedded" within an element, such as within a wall of a needle or catheter tube, have an input surface that may not be exposed (e.g. a temperature sensor that senses ambient temperature through the wall surface) or may be exposed (e.g. a pH sensor having an input surface that is in fluid communication with an interior surface or an exterior surface of a catheter tube).

In an example, the catheter assembly 104 can have at least one sensor for sensing and/or monitoring patient conditions such as temperature or for sensing and/or monitoring the status of an interior or exterior environment of the catheter hub, such as for flow or pressure. As further discussed below, the one or more sensors can comprise an accelerometer to detect movement, pressure sensor, temperature sensor, position and humidity sensors, to name a few non-limiting examples, and can be used to measure and monitor blood flow, pulse, blood pressure, blood oxygen levels, body temperature, localized skin temperature, pH value, occlusion of catheter, flow rate, etc. Due to the size of typical catheter assemblies, the sensors are suitably sized and shaped accordingly and can be powered using body heat. For example, a heat to electricity converter can be used to charge a capacitor to then power a sensor for use with the devices of the present disclosure. Alternatively or additionally, a flexible supercapacitor can be used to power the sensors. Flexible supercapacitors have been discovered and described in US Publication No. 2014/0338715 and US Publication No. 2010/0051079 that can accumulate an electric charge using heat from the surroundings. Power discharged from the flexible supercapacitor can be configured to power the one or more sensors and associated modules, such as a communications module for forwarding the detected signals to a server, controller or other modules for further processing. In some embodiments, the flexible supercapacitor could be used to charge a battery or a capacitor, which is, in turn, used to power one or more electronic devices, such as a sensor or a processor.

Flexible supercapacitors are known to researchers and scientists and have been experimented with in connection with wearable electronics. These thermally chargeable solid-state supercapacitor can be made from solid-state polymer electrolytes that produce large thermally induced voltage from a heat source, such temperature that emanates from a body. The voltage can then initiate an electrochemical reaction in electrolytes for charging. The capacitor can also use traditional electrical charging method for capacitors. The sensors can be integrated into wireless data transmission system for transmitting data to a local electronic device for use with an App or to a Cloud server via a Wi-Fi gateway for viewing, recording, trending, analyzing, etc., using a web-browser dashboard. In preferred embodiments, the flexible supercapacitor is coupled to an element of the catheter that is directly coupled to the patient, such as wings 150a or 150b of catheter hub 110, or to a portion of catheter tube 152.

With reference again to the system 100 of FIG. 1, the sensor equipped catheter assembly 104 can embody a catheter device as shown in U.S. Pat. Nos. 8,382,721; 8,540,728; and 8,597,249, the contents of which are expressly incorporated herein by reference. The catheter assembly 104 can include one or more sensors 106 located with the catheter hub 110, the needle hub 112, or both. The sensors can be located internally of the catheter hub and the needle hub and/or externally of the catheter hub and the needle hub depending on the conditions to be sensed and the type of data to be acquired. In some examples, a needle guard can be provided with the catheter assembly 104 and can be located outside of the catheter hub, such as in a third housing located between the catheter hub and the needle hub. In other examples, the needle can be covered after successful venipuncture using a spring-loaded needle hub with a depressible tab that pushes the needle hub and needle into a protective barrel or sheath.

The one or more sensors 106 can be integrated with a Bluetooth Low Energy (BLE) module 114 for communicating with a local smart device 120 having Bluetooth connectivity to communicate data sensed or picked up by the one or more sensors 106 to the local smart device. The local smart device 120 can include a server, a laptop computer, a desktop computer, a handheld device, such as a smartphone or a tablet, or combinations thereof. Custom program software can be provided with the local smart device 120 to process and display the sensed data and to enable manipulation of the data for any number of views and reports, such as to spot trends, to track high or low set points, etc. As Bluetooth communication has a limited range, the local smart device is typically located within 15-20 meters from the catheter assembly 104 to ensure strong wireless connectivity between the catheter assembly and the smart device 120.

Figure 8C:
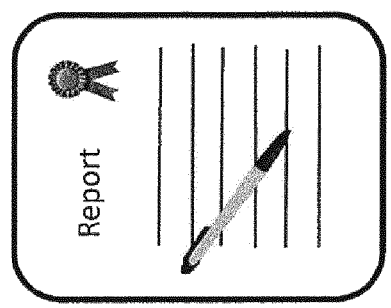
FIGS. 8A, 8B, and 8C depict exemplary reports that can be generated using the system of the present disclosure to gain information regarding an infusion therapy treatment using a catheter assembly equipped with one or more sensors.
Figure 8B:
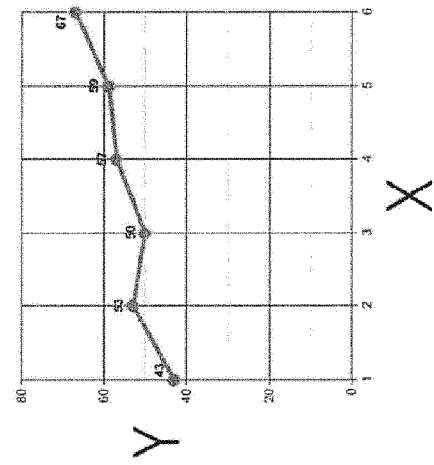
Figure 8A:
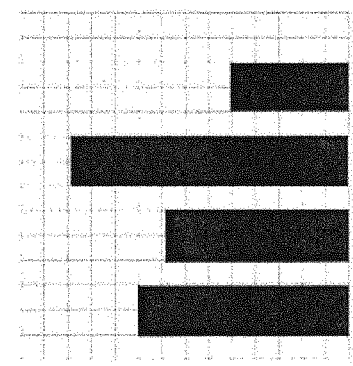

Alternatively or additionally, the catheter assembly 104 may communicate with a Cloud server 130 via a gateway 140, which can be dedicated for the catheter system. In an example, the gateway 140 may incorporate both a BLE module 142 and a Wi-Fi module 144. Communication between the catheter assembly 104 and the gateway 140 can be via BLE connectivity and between the gateway 140 and the Cloud server 130 via Wi-Fi, such as using Wi-Fi to communicate to a router to then communicate to the Cloud. Data sensed, collected, or picked up by the one or more sensors on the catheter assembly 104 can therefore be transmitted to the Cloud server 130 for recording, monitoring, analyzing and/or viewing via the gateway 140. In some examples, a BLE mesh network can be provided to extend the range between the catheter assembly 104 and the gateway 140. In an example, the Cloud server is provided with data analytics and a web-browser dashboard to analyze uploaded data for usable information, such as to spot trends, patterns, and cause-effect relationships of the various detected conditions. Reports can be generated of the information uploaded and collected, such as provided in a bar chart form as shown in FIG. 8A, in a line chart form as shown in FIG. 8B, or in a text or written report form as shown in FIG. 8C, or combinations thereof.

A clinician or an individual authorized by the patient, as provided by health and hospital policies, can view data stored on the Cloud server 130 using a web-browser dashboard and a smart device 120 from anywhere internet connectivity is available. Proper security and authentication may be required before the clinician and the authorized user can view the stored data.

With reference now to FIG. 2, a catheter hub 110 is shown looking at the bottom of the pair of wings 150a, 150b with the needle and needle hub removed therefrom. The catheter hub 110 has a catheter tube 152 attached to the distal end of the hub body 156 and has a proximal inlet or opening 154 at an opposite end having a Luer taper for receiving a male Luer tip, such as a male infusion line, a syringe, or a male Luer adaptor. As further discussed below, one or more sensors 106 can be incorporated with the catheter assembly 104 of the present embodiment, such as to the catheter tube 152, to the hub body 156 of the catheter hub 110, to the wings 150a, 150b, or combinations thereof. One or more sensors 106 can be located interiorly of the hub body, interiorly of the catheter tube, externally of the hub body, externally of the wings, embedded in the wall of the hub body, or combinations thereof.

FIG. 3 is a schematic view showing a catheter hub 110 placed in fluid communication with a peripheral vein on a patient's hand 160 at a puncture site 162, shown without any fluid line connected to the catheter hub. In some examples, rather than connecting to the peripheral vein at the hand, the puncture site can be at the forearm or elsewhere, such as near the chest for a central venous catheter or at the upper arm area for a PICC or midline catheter. The catheter hub 110 can be secured to the hand 160 using a medical dressing 164, shown in dashed-lines, which is secured to the hand via adhesive. Alternatively or additionally, the medical dressing 164 can be incorporated with the wings 150a, 150b without separately using adhesive, tape, or bandages to secure the catheter hub to the hand. One or more sensors of the present disclosure can be mounted to the exterior of the catheter hub, such as when mounting an accelerometer to the wings to detect movement of the catheter hub or the hand. In other examples, sensors can be mounted to the interior of the catheter hub, in the wall of the catheter hub, or in the lumen of the catheter tube to detect patient conditions, such as pH value, oxygen value, or local temperature.

In some examples, electronic components of the present system can be located both internally and externally of the catheter hub and the catheter tube. For example, the wireless module and the power module can both be located on the exterior of the catheter hub for powering the various sensors and modules and for sending collected signals to a local smart device or to the Cloud server. Sensors mounted in the interior of the hub body are thus in fluid communication with fluid passing through the catheter hub, including IV fluid and blood, while other modules, for example non-sensor modules, can be located externally and not be subjected to any wet or liquid environment.

As further discussed below, one or more sensors 106 can be coupled with the catheter hub to sense, detect, and/or monitor various conditions about the patient, such as body or local temperature, blood temperature, blood pH level, and/or about the status of the catheter hub 104, such as whether the hub body 156 has moved (e.g. by triggering an alert when an accelerometer detects movement in a direction), whether a flow rate is detected through the catheter hub (e.g. by measuring flow rate or pressure), etc. Thus, the present catheter assembly 104, such as the catheter hub 110 of the present catheter assembly, is configured to not only serve as a vehicle for fluid infusion therapy but can also include one or more sensors to provide data on a number of different conditions that can be used by a clinician to gauge the effectiveness and various other aspects of the infusion therapy.

Figure 4:
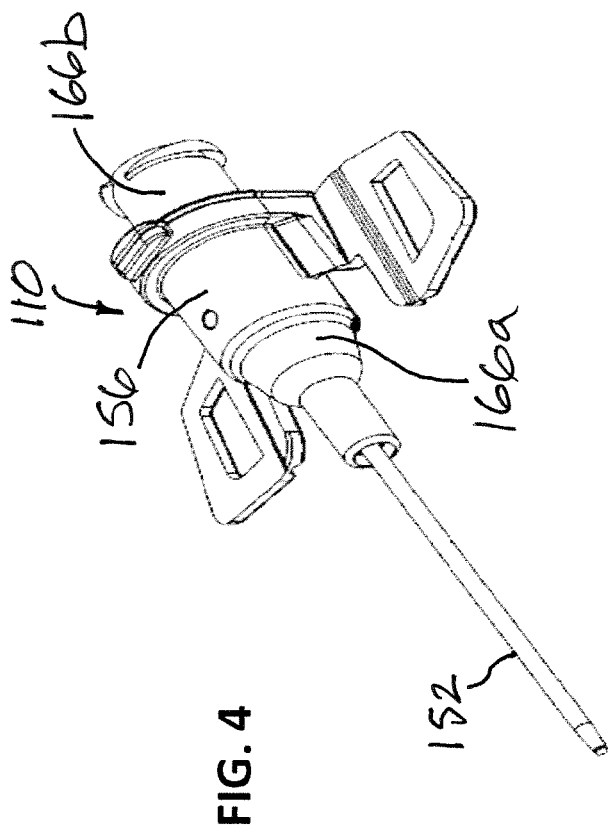
FIG. 4 is a perspective view of a catheter assembly shown without the needle and needle hub and with a multi-part hub body.

With reference now to FIG. 4, a perspective view of a catheter hub 110 is shown with yet different shaped wings. The catheter hub 110 is shown with a hub body 156 having a first hub section 166a attached to a second hub section 166b. In the present embodiment, the two hub body sections provide convenient access to the interior of the hub body 156 to facilitate mounting the one or more sensors 106 and optionally other components, such as a valve and a valve opener, inside the hub body. After the one or more sensors, as well as after any valve, valve opener, and needle guard, where applicable, are mounted, the two hub body sections can be joined and secured to one another by adhesive, bonding, welding, or combinations thereof.

A catheter tube 152 is shown attached to the distal end of the first hub section 166a using conventional means, such as with a metal bushing. In some examples, the catheter hub 110 can be an integrated infusion catheter having a side fluid port extending from the hub body with a tubing attached to the fluid port and a fluid adaptor attached at the opposite end of the tubing, such as a needleless connector. A septum can be located on the inside of the hub body of the integrated infusion catheter, proximal of the fluid port and distal of the proximal catheter hub opening. In alternative embodiments, the catheter hub can include a unitarily formed port, also referred to as a ported catheter, for receiving a male Luer tip directly, without the flexible tubing.

Figure 5:
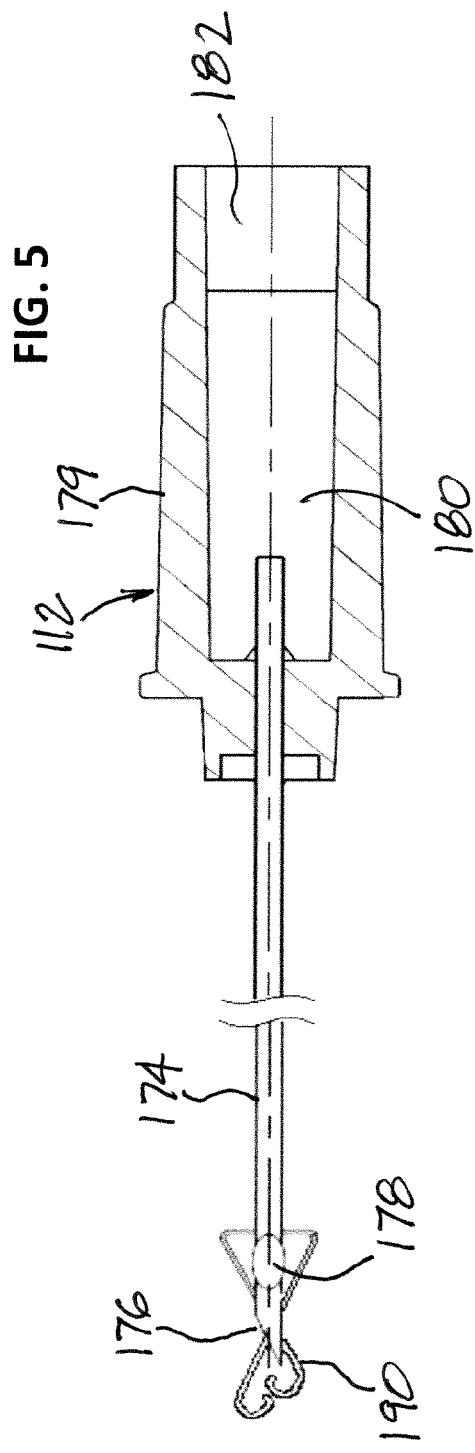
FIG. 5 is a cross-sectional side view of an exemplary needle hub and needle having change in profile interacting with a needle guard for covering the needle tip.

FIG. 5 is a schematic cross-sectional view of a needle hub 112 having a needle 174 with a needle tip 176 and a change in profile 178, which can be a crimp, a bulge, a sleeve, or a material buildup, removed from the catheter hub 110 of FIG. 4, such as following successful venipuncture. The needle hub 112 has a needle hub body 179 defining an interior flashback chamber 180 with a proximal opening 182 that typically has a vent plug (not shown) attached therewith to prevent blood flashback from leaking out the proximal opening. One or more sensors can be located with the needle hub 112, such as to the interior of the needle hub body 179 to sense conditions of the blood, such as oxygen or pH levels.

A needle guard or tip protector 190 is shown at the distal end of the needle 174, surrounding or blocking the needle tip 176. Aspects of the needle guard are disclosed in U.S. Pat. Nos. 8,382,721; 8,540,728; and 8,597,249, previously incorporated by reference. In some examples, other needle safety devices or guards for preventing inadvertent needle sticks can be used with the catheter assembly with one or more sensors. For example, a spring loaded needle assembly can be activated to either push a shield over the needle in a protected position following use or the needle can be pushed into a stationary outer protective barrel for use to cover the used needle tip.

Figure 6A:
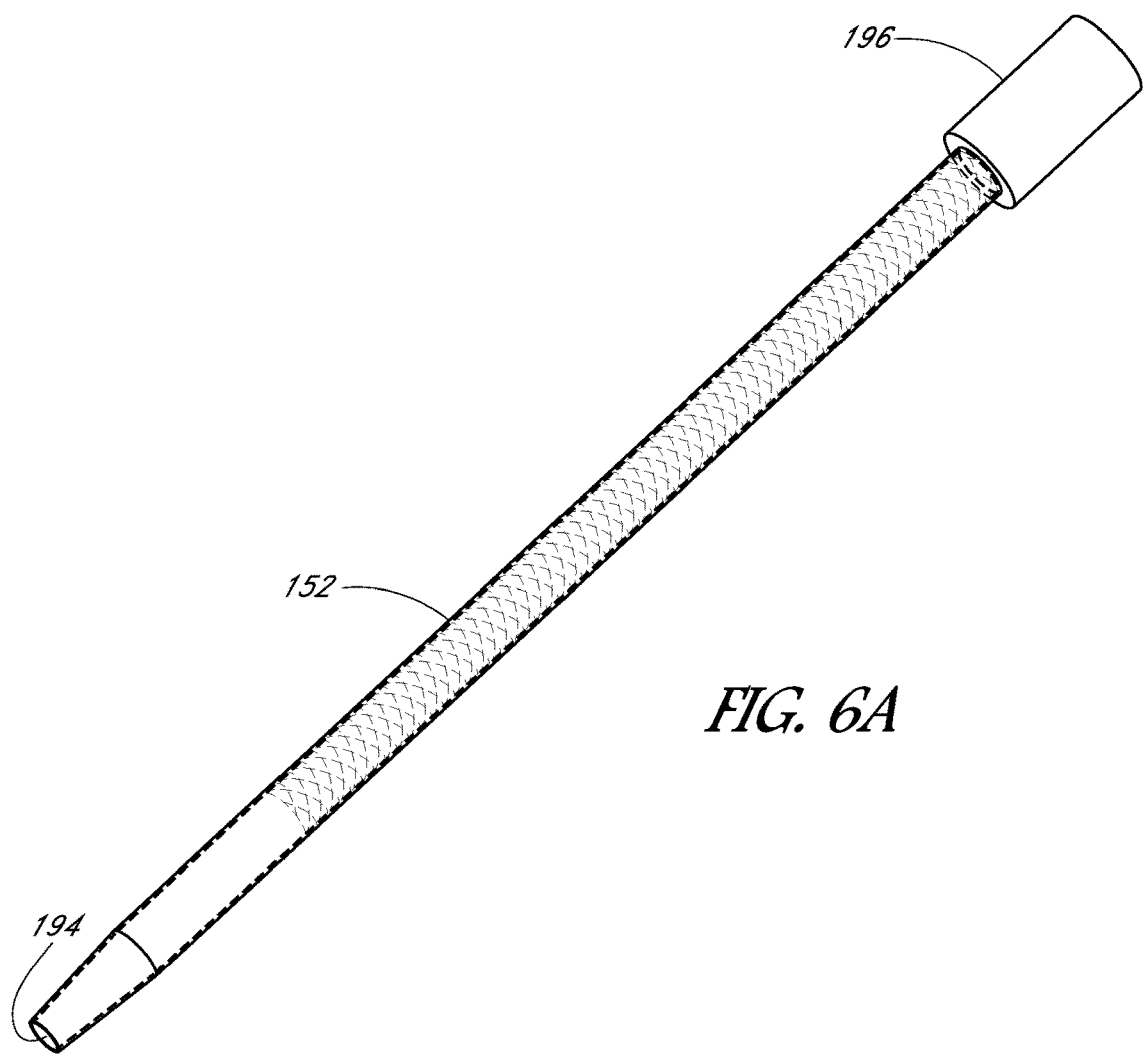
FIGS. 6A and 6B show different views of a catheter tube having a sensor material applied therewith and FIG. 6C is a cross-sectional end view of either a catheter tube or a catheter hub having one or more sensors embedded within the wall layer thereof.
Figure 6B:
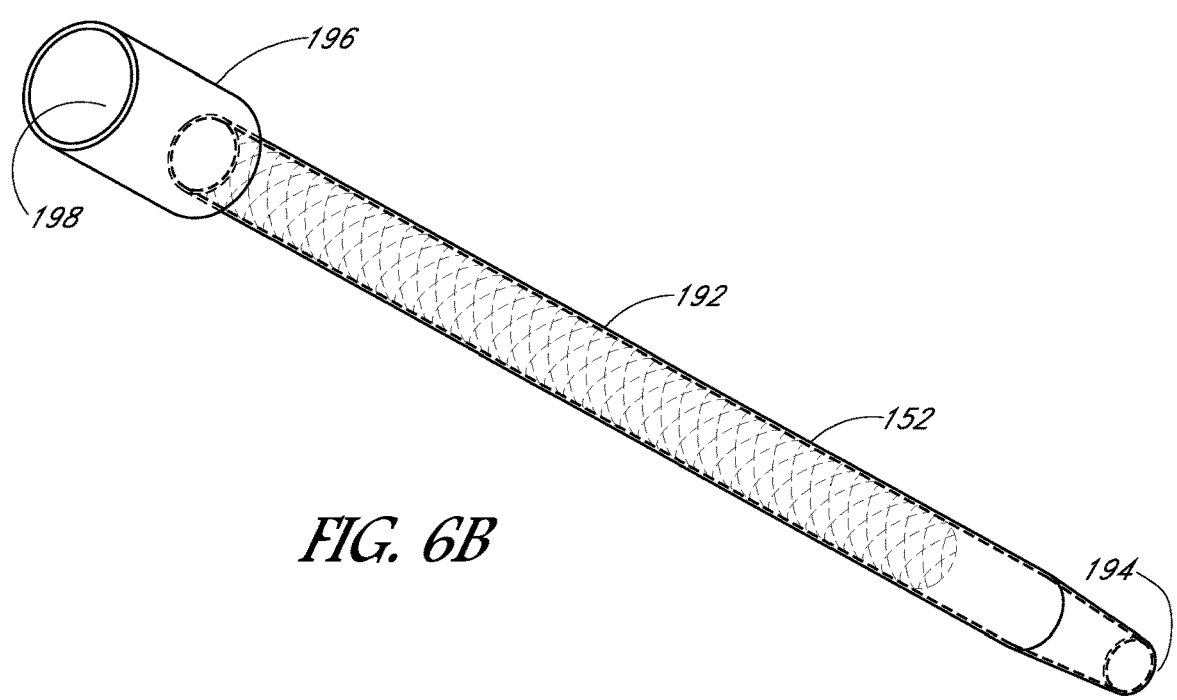

With reference now to FIGS. 6A and 6B, a catheter tube 152 is shown from different viewing perspectives. The catheter tube 152 has a body 192 with a distal opening 194, an enlarged proximal section 196 having a proximal opening 198 for receiving a metal bushing to secure the proximal section to the interior of the catheter hub, which is conventional. In an example, the interior of the tube body 192 can be lined, partially or completely, with a polypyrrole sensing material. For example, the annular space of the catheter tube body 192 can be lined with a polypyrrole sensing material for use to detect one or more of temperature, blood flow, blood pressure, blood oxygen levels, pH value, occlusion of catheter, etc. In an example, the sensing material inner layer can form a complete circumference interiorly of the outer catheter body material and can extend the length of the catheter tube or part of the length of the catheter tube.

Figure 6C:
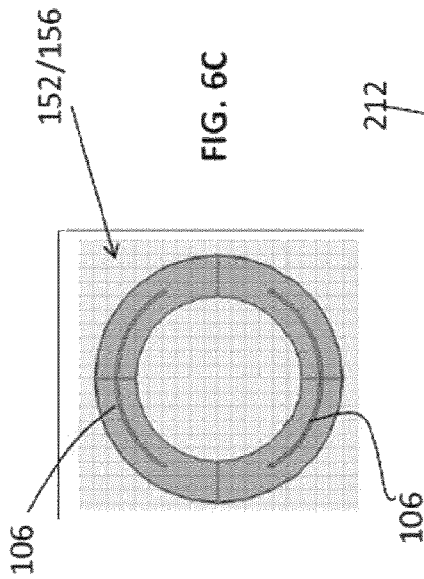

FIG. 6C is a cross-sectional end view of a structure that can be a catheter tube 152 or a catheter hub 156, shown schematically. As shown, the body of the catheter tube 152 or the catheter hub 156 can have one or more sensors 106 impregnated or embedded into the wall layer thereof. The proximal section 196 of the catheter tube can be made from a conducive metal material for acquiring signals from the sensing material and for connecting to other electronic modules, such as to a power source that utilizes heat to convert to electrical power and to a wireless signal transmitter. In some examples, the proximal section 196 can be made from a conductive polymer material, also known as intrinsically conducting polymer or polymers (ICPs). ICPs are organic polymers that are known for conducting electricity.

Figure 7:
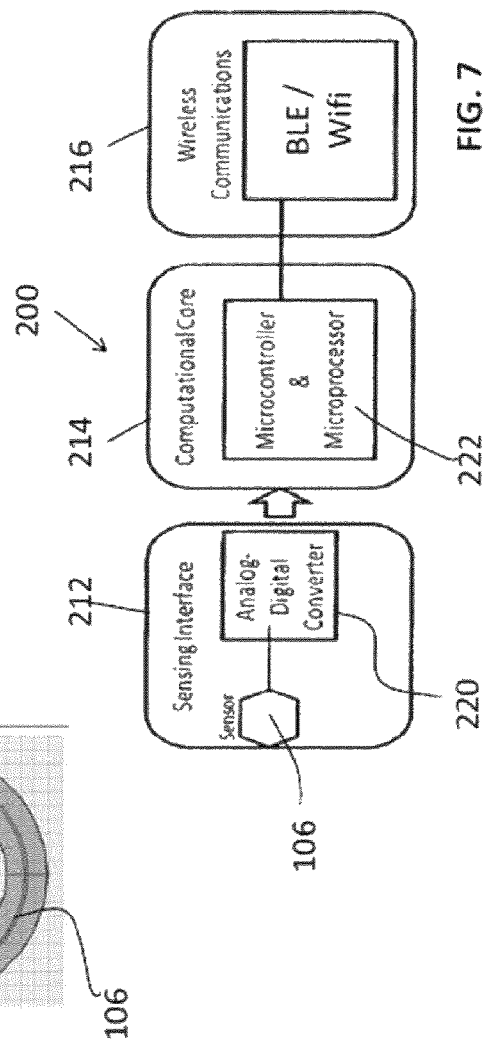
FIG. 7 is a diagram showing a sensing and transmitting architecture of the present system.

With reference now to FIG. 7, a diagram showing the sensing and transmitting architecture of the present system is shown. In an example, the system 200 comprises sensing module 212, a data processing module 214, and a communications module 216, which can be located on a catheter assembly 104 or across several platforms, such as on a catheter assembly and in nearby peripheral equipment. Although not shown, a power module that uses heat to electricity conversion is incorporated to energize the various sensors.

The sensing module 212 can comprise one or more individual sensors 106 for detecting any of the various parameters and conditions noted elsewhere herein. Individual sensors can be positioned inside the interior of the catheter body, the lumen of the catheter tube, and/or the interior of the needle hub. Individual sensors can also be mounted externally of the catheter hub body, such as on the wings of the catheter hub, on the hub body, and/or on the medical dressing. For example, an accelerometer may be mounted on the wings of the catheter hub to detect movement and a temperature sensor maybe used to detect surface skin temperature or local temperature of the patient.

The sensing module 212 can include an analog to digital converter 220 (A/D converter) for converting analog signals to digital signals. Optionally, the analog signals are simply communicated to a smart device or to the Cloud server, via a communications module, to be processed, converted, manipulated, etc. away or remote from the catheter assembly. For example, analog to digital conversion can be performed on the Cloud server. This allows the system of the present disclosure to operate on low power requirements and can be less costly to implement if the analog to digital converter can be processed elsewhere.

The present system 200 can comprise a data processing module 214 having a controller 222, which can comprise a microcontroller and/or a microprocessor, embodied in a printed circuit board (PCB). The data processing module 214 can be provided with firmware and software to process the digital signals from the A/D converter to then perform one or more functions related to the processed signals, such as to send signals to a smart device, to the Cloud server via a gateway, etc. Optionally, the data processing can be processed by the smart device or by the data analytics on the Cloud server. In preferred embodiments, the data processing module merely acts as a data queue that transmits sensor data to a transmitter, preferably a wireless transmitter such as wireless communications 216. Data processing module 214 preferably has a transient or non-transient memory that saves data received from one or more sensors and transmits them to a remote computer system, such as cloud server 130 or local smart device 120 (FIG. 1), which can process the data. In preferred embodiments, data processing module 214 adds a unique label to each data segment that uniquely identifies a sensor, such as a temperature sensor within a catheter tube and a temperature sensor within a catheter hub, allowing the receiving computer system to categorize sensor data accordingly. Such labels could be added using any suitable means, such as an XML (extended meta-language) format. For example, each packet transmitted from a transceiver could comprise a time-stamp, a series of sensor metrics, a type of each sensor, and a unique identifier for each sensor. The unique identifier could be a location or a position within the catheter that allows a data processor system to calculate distance between at least two of the sensors.

The remote computer system could then process the sensor data and perform any suitable analysis upon the data, such as compiling a data report or triggering an alert when a data threshold metric is passed, such as a blood temperature that has exceeded a threshold or fallen below a threshold, or a blood flow that has exceeded a threshold or fallen below a threshold. In some embodiments, the data processing module 214 could be configured to perform such analysis, such as triggering an LED light on the catheter when a predetermined threshold is reached. In preferred embodiments, data from a plurality of sensors could be analyzed to create metrics, for example a data metrics from a first temperature sensor at a first location and a second temperature sensor at a second location could be utilized to calculate how the temperature differential between blood measured from the first temperature to the second location.

The present system 200 can comprise a data communication module 216 for communicating sensed signals to a smart device or to the Cloud server using any suitable wireless transceiver, such as BLE connectivity devices and Wi-Fi. Using data analytics, the signals can be displayed via charts, tables, and/or report format on the PC, laptop, mobile device.

Sensors discussed elsewhere herein can be made from materials that can include polypyrrole, carbon nanotubes, glass carbon, and polyacrylonoytile (PAN). The one or more sensors incorporated with the catheter assembly of the present embodiment, or to components thereof, can be connected, physically or wirelessly, to a wireless data transmitting component, such as to a BLE module, to transfer collected data to a smart device or a Cloud server for use by data analytics, an App, or a web-browser dashboard to analyze the uploaded data for usable information, such as to spot trends, patterns, and cause-effect relationships of the various detected conditions. In some examples, a fiber optic sensor can be used as a sensing element, also known an intrinsic sensor, or as means for relaying signals from a remote sensor to the electronics that process the signals, also known as an extrinsic sensor. A fiber optic sensor can be used to measure strain, temperature, pressure and other quantities. Thus, aspects of the present disclosure is understood to include usage of a fiber optic sensor for both intrinsic sensor purposes, for extrinsic sensor purposes, or for both purposes.

For the catheter assemblies with sensors and assembly components disclosed herein, it is understood that where a feature is shown but not expressly described and is otherwise the same or similar to the feature or features described elsewhere, such as above with reference to FIGS. 1-7, the disclosed part or parts shown in all the drawing figures but not expressly described because of redundancy and because knowledge is built on a foundation laid by earlier disclosures may nonetheless be understood to be described or taught by the same or similar features expressly set forth in the text for the embodiments in which the feature or features are described. Said differently, subsequent disclosures of the present application are built upon the foundation of earlier disclosures unless the context indicates otherwise.

The disclosure is therefore understood to teach a person of ordinary skill in the art the disclosed embodiments and the features of the disclosed embodiments without having to repeat similar components and features in all embodiments since a skilled artisan would not disregard similar structural features having just read about them in several preceding paragraphs nor ignore knowledge gained from earlier descriptions set forth in the same specification. As such, the same or similar features shown in the following catheter assemblies incorporate the teachings of earlier embodiments unless the context indicates otherwise. Therefore, it is contemplated that later disclosed embodiments enjoy the benefit of earlier expressly described embodiments, such as features and structures of earlier described embodiments, unless the context indicates otherwise.

With reference now to FIG. 9A, a schematic cross-sectional side view of an alternative catheter assembly 104 is shown with a catheter hub 110. The catheter assembly 104 is shown without a needle hub and needle for clarity but is understood to be part of the catheter assembly for use to gain intravenous access. The needle can instead be a stylet, or a solid needle shaft. In some examples, a guidewire is used with the catheter assembly to help guide placement of the catheter tube. As shown, the catheter hub 110 has a catheter hub body 156 and a catheter tube 152 with a tube body 192 attached to the hub body, such as with a metal bushing 250. In an example, the interior of the tube body 192 can be lined, partially or completely, with a sensing material 106, such as a polypyrrole sensing material. For example, the annular space of the catheter tube body 192 can be lined with a polypyrrole sensing material 106 for use to detect one or more of temperature, blood flow, blood pressure, blood oxygen levels, pH value, occlusion of catheter, etc. In some examples, the sensor 106 can be embedded inside the thickness of the catheter tube as shown in FIG. 6C.

Similar to the catheter tube 152 described with reference to FIGS. 6A and 6B, the present catheter tube has a body 192 with a distal opening 194 and a proximal section 196 made from a conducting material. In some embodiments, the body 92 could comprise one or more sensors embedded within an insulating material electronically coupled to the conductive proximal section 196 via an insulated path, such that conductive proximal section can abut an input port of an electronic device, such as an A/D converter or an input to a data processing module. Alternatively, the proximal section can be made from a polymer material and is lined with a sensing or conducting material, as further discussed below. The distal opening 194 can have a reduced opening compared to other sections of the catheter tube to form a seal around the needle shaft or stylet. The proximal section 196 of the catheter tube 152 can be made from a conducive material for acquiring signals from the sensing material 106 lining the interior of the tube body 192 and for connecting to other electronic modules, such as to a power source that utilizes heat to convert to electrical power and to a wireless signal transmitter. Alternatively, the sensing material can extend past the proximal section 196 and an electrical connector is used to couple the sensor 106 to other devices.

In some examples, the proximal section 196 can be made from a conductive polymer material, also known as intrinsically conducting polymer or polymers (ICPs). ICPs are organic polymers that are known for conducting electricity. The sensor material can be made from materials that can include polypyrrole, carbon nanotubes, glass carbon, and polyacrylonoytile (PAN). In some examples, the sensing material 106 at the tube body and the sensing material at the proximal section 196 of the catheter tube 152 can be integrally formed or can be singularly formed.

With further reference to FIG. 9B in addition to FIG. 9A, an enlarged view of the connection between the sensor 106 with the catheter tube 152 and the conductor 290 with the catheter hub body 156 is shown. In an example, electrical communication between the sensor 106 located with the catheter tube 192 and the conductor 290 located with the catheter hub 110 can be provided through or by using an electrical connector 260. In an example, the electrical connector 260 is made from a conductive polymer material, such as from ICPs, polypyrrole, carbon nanotubes, glass carbon, and polyacrylonoytile (PAN). In other examples, the electrical connector 260 is made from a conductive metal material, such as from copper, brass, or their alloys. One or more optic fibers can alternatively be used for the sensor 106 and/or the conductor 290, as previously discussed.

The connector 260 can have a body portion 262 and a flange portion 264 having a gap 266 therebetween. The body portion 262 can contact or wedge against the sensor 106 with the catheter hub 110. Part of the sensor 106 with the catheter tube 152 can be positioned in the gap 266. Once a metal bushing 250 (FIG. 9A) is pushed into the catheter hub 110 to wedge the catheter tube 152 between the catheter hub and the metal bushing, the flange 264 will clamp against the proximal end of the catheter tube sensor 106 of the catheter hub and the body portion 262 of the electrical connector 260.

In an example, the catheter tube sensor 106 has a proximal end 270 that is longer than the proximal end of the catheter tube body 192 so that a folded section 272 of the catheter tube sensor 106 is folded around the exterior of the catheter tube body to directly contact the body portion 262 of the connector 260. This folded section 272 allows the catheter tube sensor 106 to directly contact the body section 262 of the connector rather than only through the contact with the flange 264.

With reference again to FIG. 9A, an electronic connector assembly 280 is shown attached to the proximal end of the catheter hub body 156. The electronic connector assembly 280 can comprise a connector housing 282 and an electrical module 284. Said connector housing 282 can attach to the proximal end of the catheter hub 110 for mounting the electronics module 284 for use with the sensor 106 and the conductor 290. In some examples, fiber optic sensors can be mounted with the catheter tube and coupled to the connector assembly 280. The connector housing 282 can be made from a thermoplastic material and can have a male tip 292 for inserting into the proximal opening of the catheter hub 110 and a threaded collar for threaded engagement with external threads on the catheter hub. In other examples, the connector housing 282 can be secured to the catheter hub 110 using different securing means, such as by adhesive, detents, bonding, welding or combinations thereof. The connector housing 282 can be elongated and can have a Luer taper 286 for receiving a male Luer tip and can include external threads 288 for a threaded Luer connection.

A conductor 290 can also extend externally of the body of the connector 282 to present a surface for contacting the conductor 290 mounted with the catheter hub 110. The male tip 292 of the connector 282 can be sized and shaped to wedge the two conductors 290, 290 into good solid contact and provide a seal at the interface thereof from fluid flow. The contact between the conductors 290 at the interface of the catheter hub and the electronic connector assembly 280 allows for electrical communication of the electrical module 284 to the sensor 106 of the catheter tube. In an example, the electronic module 284 can include a sensing interface, a communication interface, and a power source, as described elsewhere herein. A cover 296 can be provided around the electric module 284 to seal the module from damage or unwanted exposure. In an example, the cover 296 can be a coat or layer of a silicone material or a sleeve.

Figure 10:
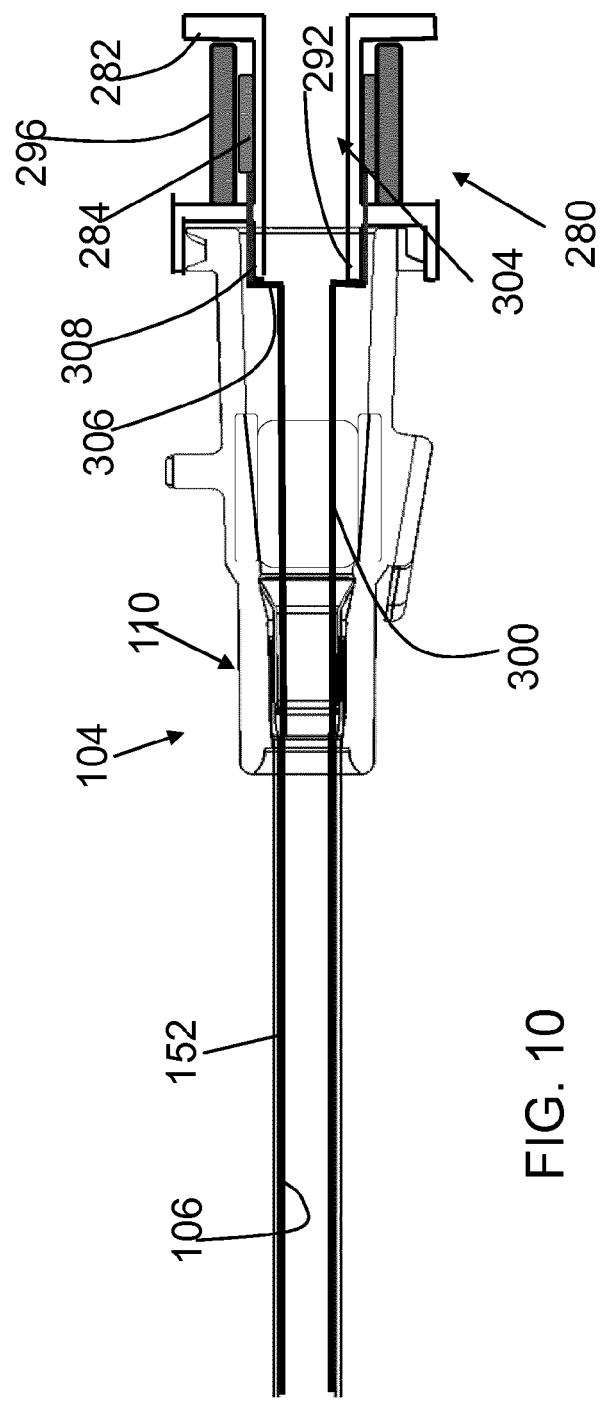
FIG. 10 is a schematic depiction of a catheter assembly comprising a sensor and an electrical connector assembly for collecting and transmitting data.

With reference now to FIG. 10, another alternative catheter assembly 104 is shown, similar to the catheter assembly of FIG. 9A and shown without a needle and needle hub. In the present embodiment, a conductor 300 contacts the sensor 106, directly or indirectly, inside the catheter tube 152. The conductor 300 can be used as an extension or a coupling to couple the sensor 106 inside the catheter tube to the electrical connector assembly 280, which comprises a connector or connector housing 282, an electrical module 284, and a cover 296, similar to the electrical connector assembly 280 of FIG. 9A. In the present embodiment, the conductor 300 is provided with a receiving end 304, which can be one of a receptacle 306 or a plug 308. The tip 292 of the connector 282 can be provided with the other one of the receptacle 306 or the plug 308. The receptacle 306 connects to the plug 308 to provide an electrical path between the conductor 300 and the electrical module 284. Alternatively, a fiber optic sensor can be incorporated with the catheter tube and an optical transmission fiber is used to connect the sensor to the electrical connector assembly 280. In an example, the electrical assembly 280 can be detachable from the catheter hub 104 to disconnect the receptacle 306 and the plug 308. The detachable configuration allows the electrical connector assembly 280 to be detached from the catheter hub and re-used or re-purpose, such as with a different catheter assembly.

Figure 11:
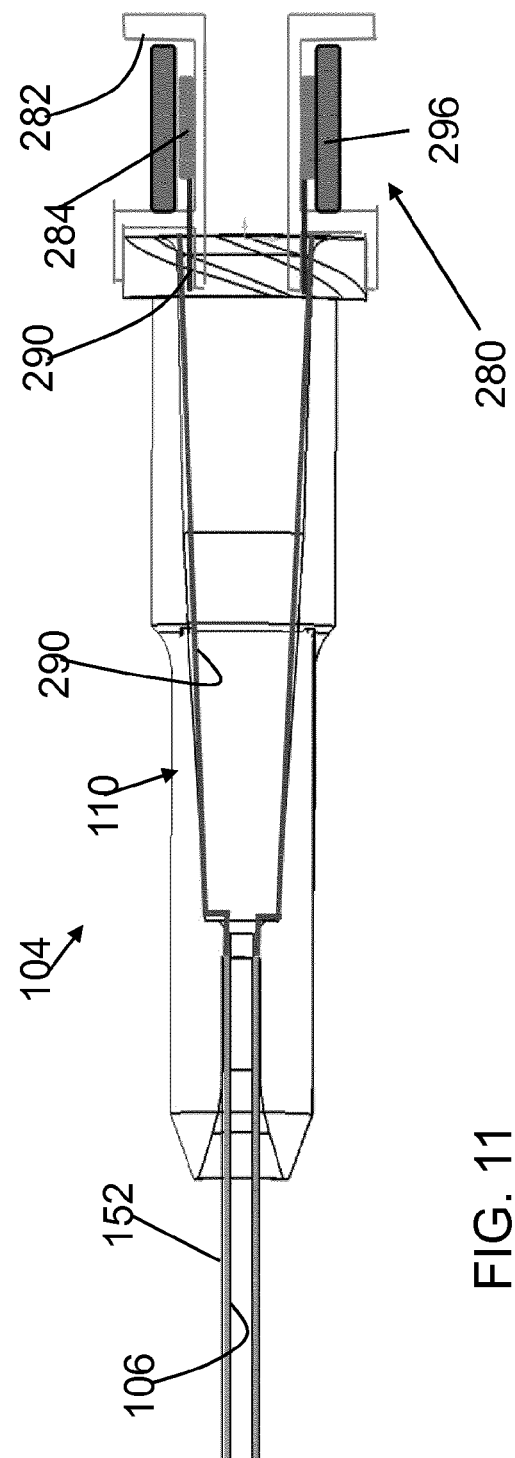
FIG. 11 is a schematic depiction of a catheter assembly comprising a sensor and an electrical connector assembly for collecting and transmitting data.

FIG. 11 shows another alternative catheter assembly 104, similar to the catheter assembly of FIG. 9A and shown without a needle and needle hub. However, like the electrical connector assembly 280 of FIG. 10, the present connector housing 282 of the electrical assembly is detachable from the proximal end of the catheter hub. The disconnection is possible by providing a connection between the sensor 106 at the catheter tube and the conductor 290 of the electrical assembly 280 with a conductor 290 of the catheter hub 110. A pressed fit or contact fit may be used to removably fix the connector 282 to the catheter hub with threading via the threaded collar on the connector engaging the threads on the catheter hub.

Figure 12:
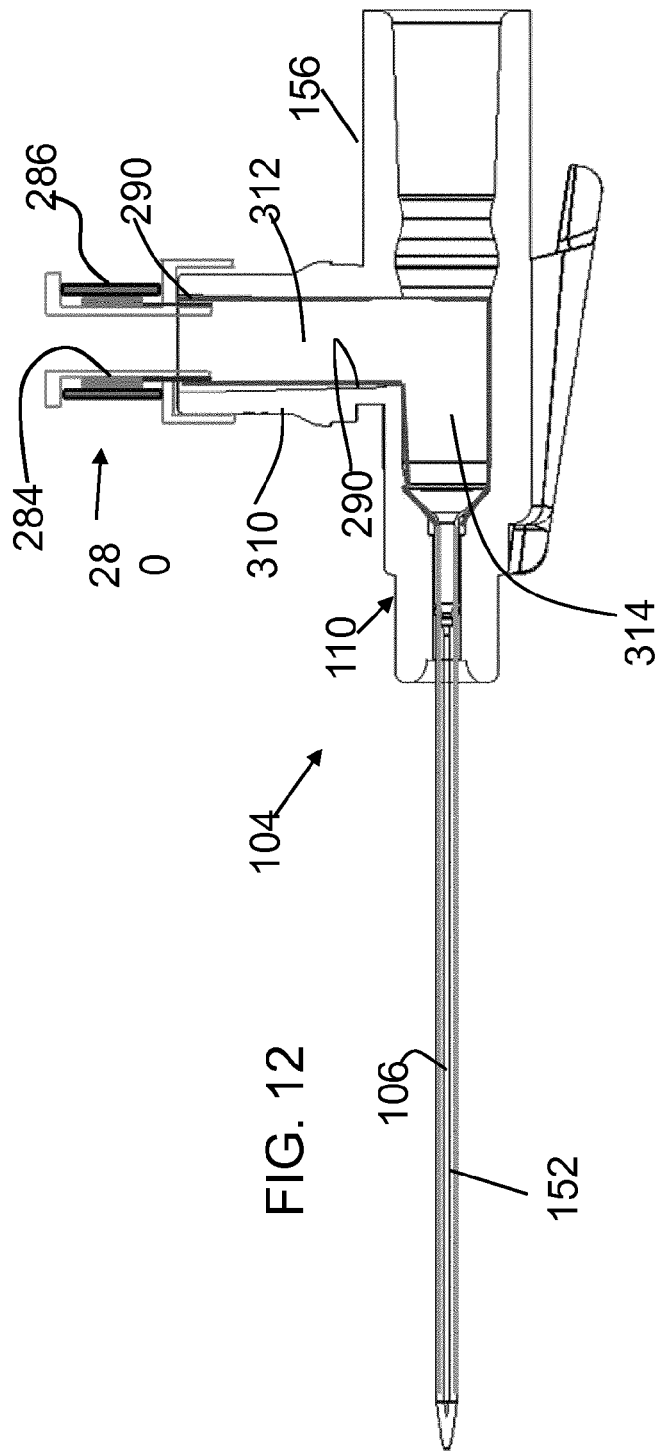
FIG. 12 is a schematic depiction of a catheter assembly comprising a sensor and an electrical connector assembly for collecting and transmitting data and wherein the catheter hub comprises a side port.

FIG. 12 shows another alternative catheter assembly 104, similar to the catheter assembly of FIG. 9A with a few exceptions, and shown without a needle and needle hub. In the present embodiment, the hub body 156 includes a side port 310 having a channel or flow path 312 in fluid communication with the interior cavity 314 of the catheter hub 110. Although not shown, a valve in the form of a sleeve may be placed in the interior of the catheter hub to block the fluid path way at the intersection of the channel 312 and the interior cavity 314. The sleeve prevents fluid from the interior cavity from leaking out through the side port 310. However, fluid pressure flowing through the side port 310, such as from a syringe or a drip line, can collapse at least part of the sleeve to allow fluid to flow into the channel 312 to flow into the interior cavity 314 and out through the catheter tube. A valve and a valve opener may be located in the proximal section of the interior cavity, as previously discussed with other catheter embodiments. In some examples, the sleeve and the valve can be a singularly or unitarily formed structure. The valve can be located proximally of the collapsible sleeve.

As shown in FIG. 12, a sensor 106 can be placed inside the catheter tube 152 for connection with an electrical connector assembly 280 via conductors located in the catheter hub body 156 and in the side port 310. In an example, the sensor 106 can be separately formed in the catheter tube then connected to the electrical connector assembly 280 using an electrical conductor. In some examples, fiber optic as an extrinsic sensor can be used to relay signals. Alternatively, the connector can be formed continuously using a conductive polymer material, polypyrrole, carbon nanotubes, glass carbon, and polyacrylonoytile (PAN).

As shown, an electrical connector assembly 280 comprising a connector housing 282, an electrical module 284, and a cover 296, similar to the electrical assembly 280 of FIG. 9A, is shown attached to the side port 310. Like the electrical assembly 280 of FIG. 10, the present connector 282 of the electrical assembly 280 is detachable from the side port 310 and can be refurbished or re-used with different catheter hub. The disconnection is possible by providing a connection between the sensor 106 and the conductor 290 of the electrical assembly 280 that is pressed fit or contact fit and held removably fixed by the connector 282 engaging the side port 310 of the catheter hub, such as by threading the threaded collar on the connector with the threads on the catheter hub.

Figure 13:
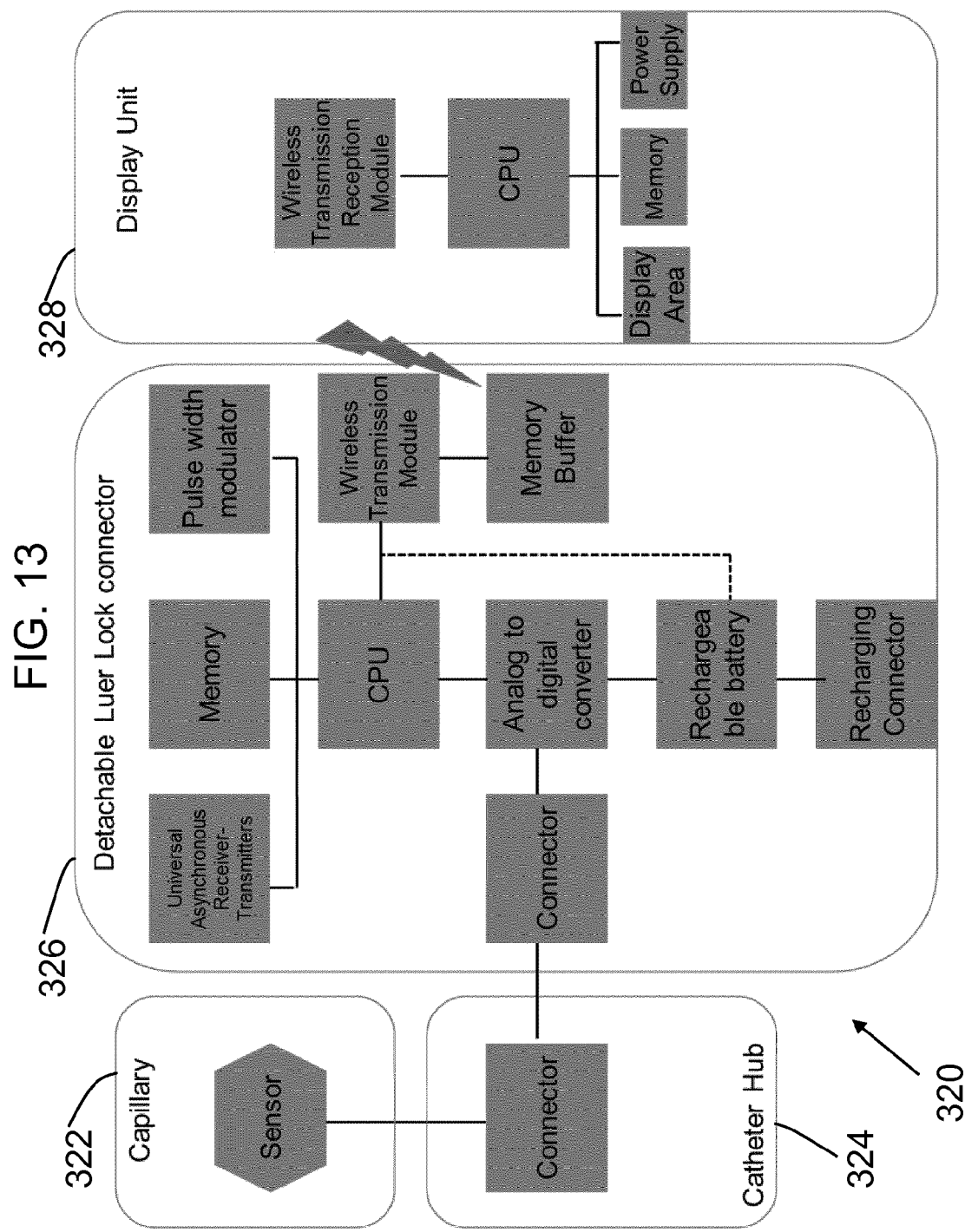
FIG. 13 is a schematic flow diagram depicting an IV catheter system comprising a catheter assembly and electronics for monitoring conditions.

With reference now to FIG. 13, a schematic flow diagram depicting a catheter system 320 comprising a catheter assembly and electronics for monitoring conditions of a patient and/or the status of the catheter device of the present invention. The system comprises a capillary or catheter tube having one or more sensors at block 322 connected to a catheter hub body at block 324, which has a connector connected thereto, such as the electrical connector assembly 280 of FIGS. 9A-12.

Block 326 depicts electronics and components that may be incorporated with the electrical connector assembly 280 for sensing and monitoring various status and conditions of the peripheral venous catheter and/or patient. As shown, the electronics can include an A/D converter for converting signals from the sensor or sensors mounted to the catheter hub and/or the catheter tube, as previously discussed. The A/D converter can be powered by a power source, which can be powered using body heat. For example, a heat to electricity converter can be used to charge a capacitor to then power the various components. Thermally chargeable solid-state supercapacitor can be made from solid-state polymer electrolyte that can produce large thermally induced voltage from a heat source, such as body temperature, to power the electronic components. In some examples, the heat to electricity converter can first charge a battery and the battery powers the electronic components.

The electrical connector assembly can further include a processor or CPU and a memory for storing and processing firmware and software. A pulse width modulator (PWM) for encoding the amplitude of a signal into a pulse width or duration of another signal for transmission and a universal asynchronous receiver-transmitter that acts as an interface to exchange data with a communications module and other serial devices can be incorporated to transmit and receive data. In other examples, a Bluetooth Low Energy (BLE) module may be incorporated to communicate using BLE signals to other BLE enabled devices, such as a smartphone, a laptop, or a tablet. In some examples, an integrated chip is incorporated with the electrical connector assembly, said integrated chip can include one or more modules, such as a communications module.

In an example, data transmitted by the electrical connector assembly at block 326 can be communicated to a dedicated gateway having both a BLE module for receiving the data through Bluetooth communication from the electrical connector assembly and a Wi-Fi module for communicating the collected data to the Cloud, which can be understood to mean cloud computing where user access from anywhere is available via the internet. Once stored on the Cloud, users can access stored information using a computing device or a handheld device, such as a tablet or a smartphone, to view and analyze the collected data.

As depicted in FIG. 13, a local display unit at block 328 can be provided for viewing, reading, and/or analyzing data collected from the electrical connector assembly. In an example, a portable viewing station comprising a maneuverable platform, such as a portable rollaway desk station, is provided with a monitor and a computing device, such as a computer or a laptop, programmed to view and process data received from the electrical connector assembly at block 326. As shown, the computing device can include a wireless transmission reception module, a CPU, a memory, a display screen or area, and a power source to power the CPU and the display screen. In some examples, a dedicated hub with memory can be stationed with the electrical connector assembly at block 326 to collect data. The dedicated hub can have connectivity, wired or wireless, to enable uploading of information contained therein to be accessed by a user, such as a doctor, nurse, or caregiver. A portable viewing station with a CPU and a monitor can be used to move from one patient room to another to access data from the dedicated hub for reviewing and analyzing patient conditions and/or equipment status.

Figure 14:
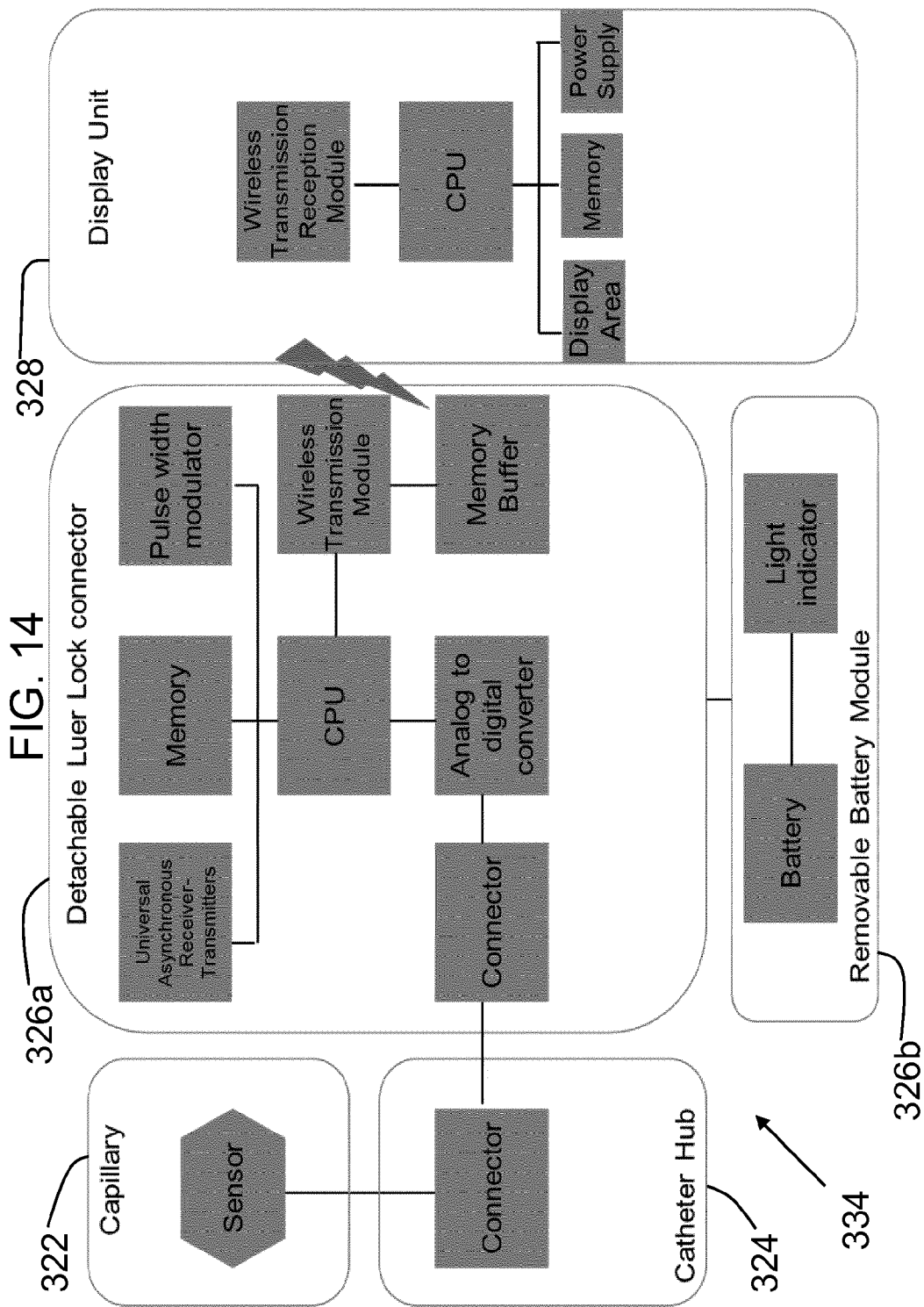
FIG. 14 is a schematic flow diagram depicting an IV catheter system comprising a catheter assembly and electronics for monitoring conditions.

FIG. 14 shows an alternative schematic flow diagram depicting an IV catheter system 334 comprising a catheter assembly and electronics for monitoring conditions of a patient and/or and the status of the peripheral venous catheter of the present invention. The system of FIG. 14 is similar to the system of FIG. 13 except the electronic connector assembly at bloc 326a does not have an integrated power supply. Instead, a removable power supply source or module is provided at block 326b for powering the electrical connector assembly. The removable power supply module can include a rechargeable battery having a light indicator for indicating the power level and firmware for controlling the power charging function. A pin connector can be provided to connect the power output of the battery to the electrical connector assembly.

With reference now to FIGS. 15A-15D, another alternative embodiment of a catheter tube 152 is shown in perspective view, cross-sectional view or end view, side view and top view, respectively. The catheter tube 152 has a body 192 with a distal opening 194, and a proximal opening 198 for receiving a metal bushing to secure the proximal section to the interior of a catheter hub, such as one of the catheter hubs described elsewhere herein. In an example, the interior of the tube body 192 can be lined, partially or completely, with a polypyrrole sensing material 106 inside a conventional catheter tube, such as one made from a polyurethane (PU) material. For example, the annular space of the catheter tube body 192 can be lined with a polypyrrole sensing material for use to detect one or more of temperature, blood flow, blood pressure, blood oxygen levels, pH value, occlusion of catheter, etc., similar to the embodiment of FIGS. 6A-6C. In the present embodiment, the sensing material 106 comprises a plurality of spaced apart or discrete sensors 106a distributed along a length of the catheter tube 152, preferably embedded within a wall of the catheter tube, as shown in FIG. 6C. For example, the discrete sensors 106a can each embody a ring shape, a round shape, an oval shape, or polygonal shape polypyrrole sensing material to enable sensing at discrete points along the catheter tube. The plurality of discrete sensors 106a can also embody a web of polypyrrole sensing material for sensing at discrete points along the catheter tube. The discrete sensors can join discrete conductive traces or conductors or can be interconnected through other sensing materials.

As used herein, sensors that are discrete from one another have separate electronic output paths that couple to a data processing module in parallel, such that data from one sensor does not corrupt data from another sensor. This allows each sensor to collect data discretely from other sensors, even if individual sensors are fungible, allowing a data processing module or computer system to compare data between multiple sensors within the same catheter system. In some embodiments, a catheter tube may comprise a plurality of discrete sensors of different types as well as different outputs. For example, the discrete sensors 106a of FIG. 15C could comprise both temperature sensors and pH sensors, and/or even pressure sensors. In some embodiments, sensors of different types could be grouped, for example in a first third of catheter tube 152, the sensors could be temperature sensors, in a second third the sensors could be pH sensors, and in a last third the sensors could be pressure sensors. The outputs of all of the sensors in a single catheter tube preferably lead to a common bus, such as an A/D converter bus, or a processor bus, allowing a processor to organize the data into a queue for transport via a transceiver.

FIG. 15B is a cross-sectional end view of the catheter tube 152 of FIG. 6A. As shown, the body of the catheter tube 152 can have one or more discrete sensors 106a impregnated or embedded into the wall layer thereof. The proximal section 196 of the catheter tube can be made from a conducive metal material for acquiring signals from the discrete sensors 106a and for connecting to other electronic modules, such as to a power source that utilizes heat to convert to electrical power and to a wireless signal transmitter. In some examples, the proximal section 196 can be made from a conductive polymer material, also known as intrinsically conducting polymer or polymers (ICPs). ICPs are organic polymers that are known for conducting electricity. In yet other examples, optic fiber sensors can be used to transmit information from the discrete sensors to an electrical connector assembly 280, as described elsewhere herein.

FIGS. 15C-15D are side and top views of the catheter tube of FIG. 15A, respectively. The discrete sensors 106a are shown distributed along the length of the catheter tube 152. In some examples, the discrete sensors can extend between 10% to 100% of the length of the catheter tube, with 20% to 90% being more preferred. The discrete sensors can be evenly spaced along a length of the catheter tube or randomly spaced along the length of the catheter tube. Here, each sensor has two discrete sensor inputs, one on a top side of catheter tube 152 and another on a bottom side of catheter tube 152, both of which lead to an output bus. Wire 106b is preferably a bus that transmits each sensor output discretely. In some embodiments, each set of up/down sensors 106a could be coupled to a common bus terminals, and in other embodiments each set of up/down sensors 106a are coupled to discrete bus terminals, allowing a data processor to compare sensor data between a sensor on a top side of catheter tube 152 and a bottom side of catheter tube 152. By coupling data sensors to a bus, this allows a data processor to compare sensor data with one another, such as a temperature at one point of the catheter tube against a temperature at another point of the catheter tube. This is particularly useful in embodiments having catheter tubes longer than a few inches, such as a one-foot catheter tube or a two-foot catheter tube. Data processing modules receiving sensor data could then glean additional data metrics via comparative analysis between received sensor data, such as pH or temperature differentials between different points along a length of a catheter tube.

With reference now to FIG. 16, another alternative catheter assembly 104 is shown, similar to the catheter assembly of FIG. 10 and shown without a needle and needle hub. In the present embodiment, a conductor 300 contacts the sensor 106, directly or indirectly, inside the catheter tube 152. The conductor 300 can be used as an extension or a coupling to couple the sensor 106 inside the catheter tube to the electrical connector assembly 280, which comprises a connector 282, an electrical module 284, and a cover 296, similar to the electrical connector assembly 280 of FIG. 10. In the present embodiment, the conductor 300 is provided with a receiving end 304, which can be one of a receptacle 306 or a plug 308 and a distal end 388 that extends into the catheter tube 152 to couple to the sensor 106 at a location inside the catheter tube. The tip 292 of the connector 282 can be provided with the other one of the receptacle 306 or the plug 308. The receptacle 306 connects to the plug 308 to provide an electrical path between the conductor 300 and the electrical module 284. In an example, the conductor 300 can instead be a fiber optic sensor for transmitting signals form the sensor 106 to the electrical connector assembly 280.

Figure 17:
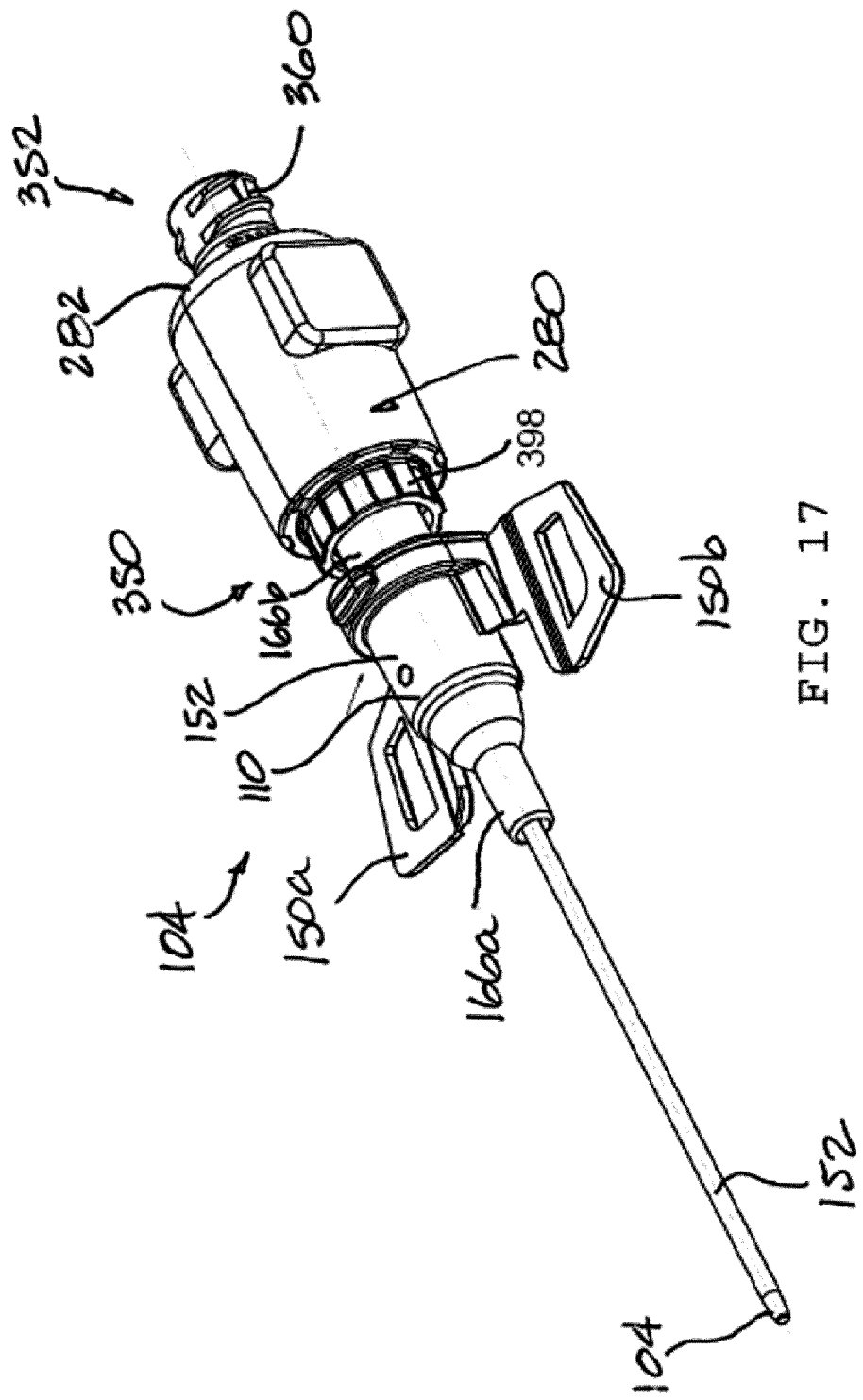
FIGS. 17-19 show an embodiment of an intravenous catheter assembly provided in accordance with further aspects of the invention.

With reference now to FIG. 17, a perspective view of a sensor equipped catheter assembly 104 is shown, similar to other catheter assemblies described elsewhere herein with a few exceptions, and shown without a needle and needle hub. In the present embodiment, the catheter hub 110 comprises a hub body 156 having a pair of wings 150a, 150b and a catheter tube 152 attached at a distal end of the hub body 156 and extending in a distal direction, terminating with a tapered distal opening 104. The hub body 156 has a first hub section 166a and a second hub section 166b, which may be referred to as a distal hub section and a proximal hub section, respectively.

An electrical connector assembly 280 is threadedly connected to the proximal hub section or second hub section 166b of the catheter hub 110. The electrical connector assembly 280 comprises a connector housing 282 having a distal end 350 and a proximal end 352. In an example, the distal end 350 comprises a collar 358 for receiving a sensor module 390, which has a collar 398 for threading to the external threads on the proximal hub section 166b. The connector housing 282 comprises an elongated open end 360 at the proximal end 352 for receiving a male Luer tip, such as an IV connector or a syringe tip. In an example, the elongated open end 360 can be a threaded female Luer. The electrical connector assembly 280 can be separated from the catheter hub 110 by un-threading the collar 398 from the second hub section 166b of the catheter hub 110.

Figure 18:
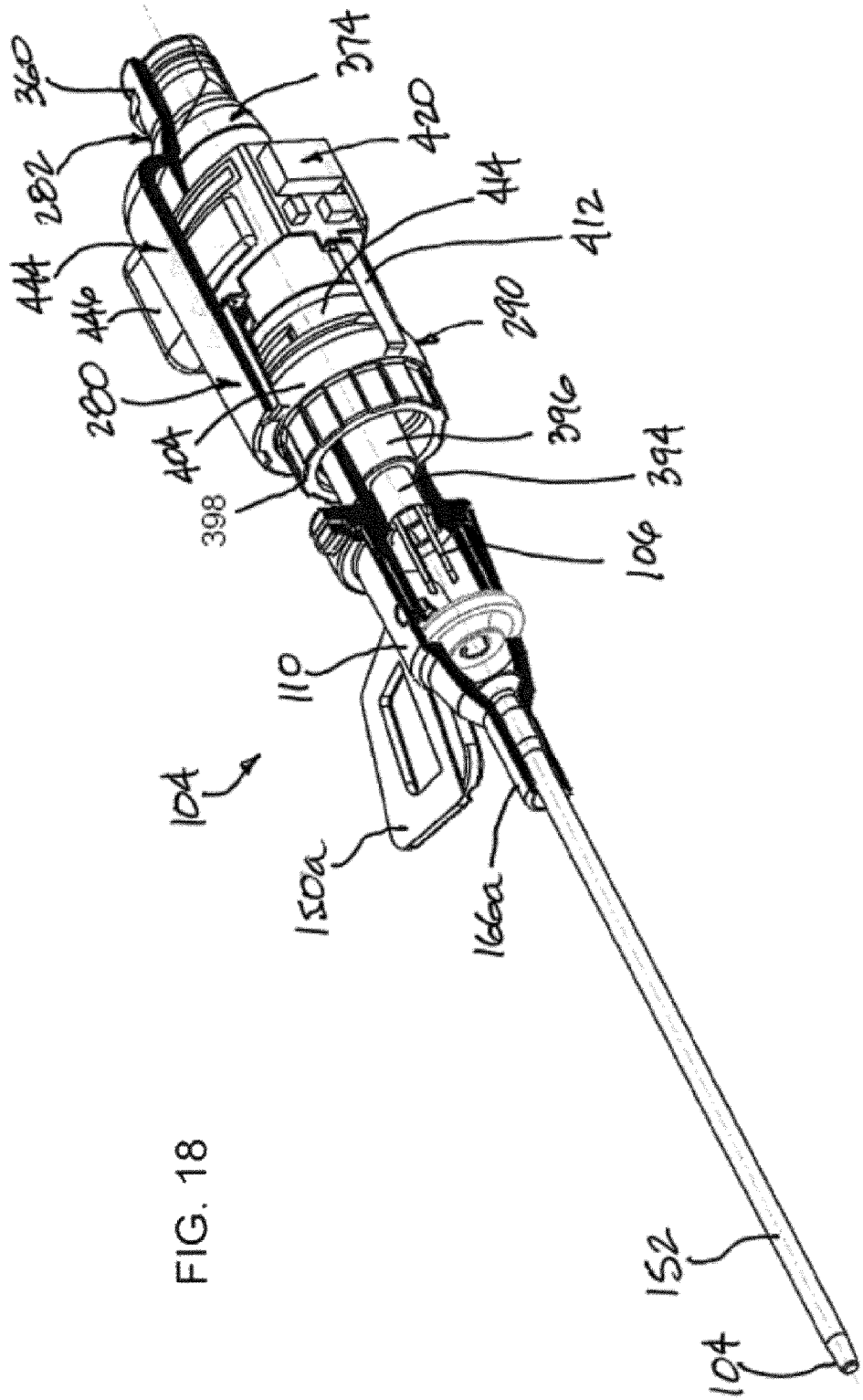
Figure 19:
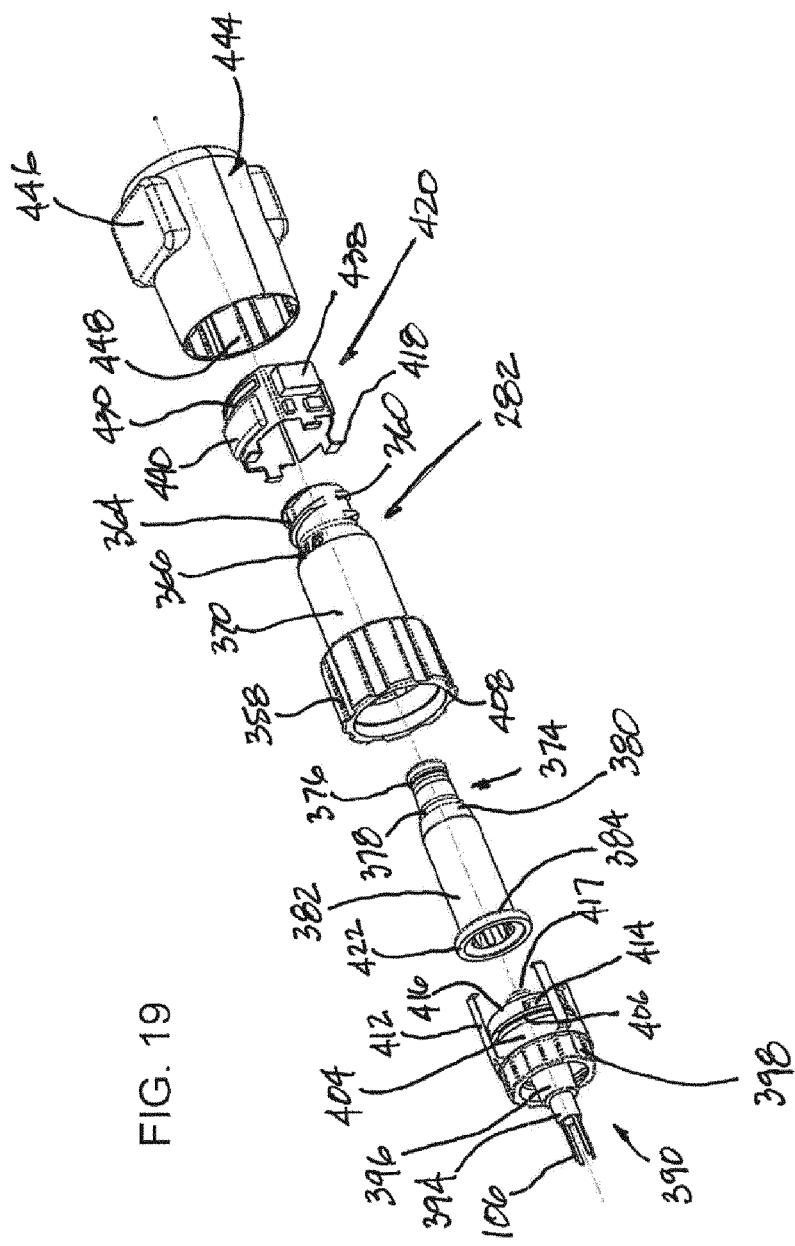

FIG. 18 shows a partial cut-away view of the catheter assembly 104 of FIG. 17 and FIG. 19 shows an exploded component view of the electrical connector assembly 280 of FIG. 17. With reference now to FIGS. 18 and 19 and further reference to FIG. 17, the connector housing 282 of the electrical connector assembly 280 is more clearly shown, which has an inlet 364, a threaded female Luer 360 at the inlet, and a collar 358 at an opposite end. In an example, the collar 358 is a slip-on collar for receiving the sensor module 390 without threading. The connector housing 282 has a body 370 with a wall structure made from a thermoplastic material defining an internal bore that is sized and shaped to receive an elastic piston 374 and a shoulder 366 located between the inlet 364 and the body 370.

The piston 374, which can fit within the bore of the housing 282, may be made from a silicone material and provided with a head section 376, a neck section 378, a shoulder 380, a body section 382, and an enlarged base 384, which can resemble a flange 386. The body section 382 and optionally the shoulder 380 can be hollow so that when the piston is located inside the housing and is pushed by a male tip inserted into the open proximal end 360 of the housing, the piston 374 collapses against the restrain of the sensor module 390. When the male tip is removed from the open proximal end 360, the piston 374 can expand or return to its less compressed state so that the head 376 of the piston 374 expands into the inside bore at the inlet section 364 to block the inlet opening 360 from fluid flow thereacross.

In an example, the combination housing 282, piston 374, and end fitting on the sensor module 390 resembles a female needleless connector. In a particular example, the combination housing 282, piston 374, and end fitting on the sensor module 390 resembles female needleless connectors disclosed in U.S. Pat. No. 7,591,449, which discloses a piston located inside a housing and wherein the piston comprises a Y-slit, among other embodiments. The combination housing 282, piston 374, and end fitting on the sensor module 390 can also resemble female needleless connectors disclosed in U.S. Pat. No. 9,695,953, which discloses a piston located inside a housing and wherein the piston comprises a spiral cut, among other embodiments. The contents of U.S. Pat. Nos. 7,591,449 and 9,695,953 are expressly incorporated herein by reference.

The sensor module 390 shown comprises central conduit 394 having a bore for fluid flow and a plurality of sensors 106, which can be the same as other sensors described elsewhere herein. The central conduit 394 can extend from a male Luer 396 to form a Luer fit with the inlet of the proximal hub section 166b of the catheter hub 110. A threaded collar 398 surrounds the male Luer 396 and is sized and shaped to threadedly engage the external threads of the proximal hub section 166b of the catheter hub 110.

A base drum 404 is connected to the collar 398 and has an outside diameter that is smaller than that of the collar 398 for insertion into the collar 358 of the housing 282. A shoulder 408 between the base drum 404 and the collar 398 of the sensor module 390 is configured to press or abut against the end edge 408 of the collar 358 of the housing 282. A plurality of electrical leads 412 are electrically coupled to the plurality of sensors 106, such as by co-molding or insert molding, and are each provided with a radial section and an axial section. The radial section of each lead 412 allows the lead to extend radially and then axially along the lengthwise direction of the housing 282 (FIG. 18) to then contact the corresponding lead 418 on the computational core 420, as further discussed below.

A head drum 414 extends from the base drum 404, which has a landing 416 and a projection 417. The projection 417 is sized and shaped to project into the open end of the piston 374 at the base 384 and the flange 422 on the base 384 is configured to press against the landing 416. A plurality of flow passages 426 are provided through the head drum 414 and in fluid communication with the bore 428 of the central conduit 394 and the male Luer 396. Thus, when the piston 374 is activated, a flow path is provided between the inlet at the head 376 and the annular space between the exterior surface of the piston 374 and the interior surface of the housing 282. The flow path is in fluid communication with the plurality of flow passages 426 at the head drum 414, and the bore 428 of the central conduit 394 and the male Luer 396. The housing 282 and the sensor module 390 may be more permanently secured to one another by bonding, welding, or both.

The computational core 420 may be mounted around the outside of the housing 282 at the body section 370. In an example, the computational core 420 comprises a body 430 having a hollow center for placement over or around the housing 282. The body 430 of the computational core 420 may be made from a dielectric material and provided with traces or leads for connection to the leads 412 on the sensor module 390 and to circuitries 438 and a power supply 440 mounted to the body 430. The power supply 440 can comprise a rechargeable battery. In an example, the circuitries 438 can comprise components discussed elsewhere herein, such as block 326 of FIG. 13, for use to relay or process sensed data from the sensors 106 located on the sensor module 390 to a remote server or processor. In an example, the computational core is separable from the leads 412 of the sensor module 390 and from the housing 282. For example, the computational core 420 can be separated for re-use after disposal of the catheter hub 110.

A protective cover 444 can be provided to cover the computational core 420, the various leads, and the various circuitries from potential damage and/or shorting. The protective cover 444 can be made from a non-conducting or dielectric material and placed over both the computational core 444 and the housing 282. In an example, the protective cover 444 can be made from a silicone material or silicone rubber and can be provided with enlarged pockets 446 and contoured surfaces 448 for placement over the computational core 444 and the housing 282 and not interfere with electrical signals and connections. Such enlarged pockets 446 and contoured surfaces 448 could allow for the body 420 to be placed within protective cover 444 in a self-orienting manner. The protective cover 444 has an open end for sliding over the computational core 444 and the housing 282 and can be made sufficiently flexible to facilitate mounting.

In use and similar to the needleless connectors disclosed in the '449 and 953 patents, when a male medical implement, such as a syringe tip or an IV connector, is connected to the inlet 364 of the housing 282, the piston 374 is compressed and a fluid path way is opened between the exterior surface of the piston 374 and the interior surface of the housing 282. The fluid pathway is also in fluid communication with the flow passages 426 at the head drum 414 and the bore 428 of the central conduit 394 of the sensor module 390. When the piston 374 is compressed as described, fluid can flow into the catheter hub 110 and the catheter tube 152 from the proximal end 352 of the housing 282, such as during IV fluid administration, or fluid can be aspirated out of the proximal end 352, such as into a barrel of a syringe.

When the male medical implement is removed from the inlet 364 of the housing, the piston is allowed to expand and the head 376 is returned to the inside area of the inlet 364 of the housing to close off the inlet from further fluid flow. Following treatment or whenever the catheter hub is replaced for a new catheter, the electrical connector assembly 280 can be removed and re-used.

Such computing assemblies that allow a computational core 444 to electronically engage with one or more conductive outputs from sensors 106 within central conduit 394 via a screw-on connection could be used to efficiently connect computational apparatuses to a catheter having a plurality of sensors. In some embodiments, a computational core could be coupled to a single catheter hub, for example an intravenous catheter hub, a midline catheter hub, or some peripherally inserted central catheters, such as those disclosed in U.S. Pat. No. 6,544,251. In catheters that have a plurality of hubs, for example a central venous catheter such as those disclosed in U.S. Pat. No. 9,504,806 or 6,723,084, each catheter hub could comprise a discrete computational core configured to wirelessly transmit sensor data to a common computer system. Catheters having a plurality of hubs that have minor branches that lead to a common main catheter branch preferably have one catheter hub having a conductive bus that couples to sensors embedded in both the main branch and minor branch of the catheter, while all other catheter hubs have a conductive bus coupled only to sensors in the associated minor branch of the catheter hub.

Methods of making and of using the sensor equipped catheter assemblies described herein and their components are within the scope of the present invention.

Although limited embodiments of catheters with monitoring capabilities and their components have been specifically described and illustrated herein, many modifications and variations will be apparent to those skilled in the art. Furthermore, elements and features expressly discussed for one embodiment but not for another may equally apply provided the functionality or structures do not conflict. Thus, unless the context indicates otherwise, like features for one embodiment are applicable to another embodiment. Accordingly, it is to be understood that the safety needle assembly and their components constructed according to principles of the disclosed devices, systems, and methods may be embodied other than as specifically described herein. The disclosure is also defined in the following claims.

What is claimed is:

1. A catheter system comprising:
   a catheter hub comprising a hub body having an exterior and an interior and an open proximal end;
   a catheter tube having a lumen attached to the catheter hub;
   a connector housing having an inlet and an outlet aligned along a lengthwise axis attached to the proximal end of the hub body;
   a movable piston having a head section, a neck section, and a body section located inside the connector housing and being configured to compress and expand to control flow through the inlet of the connector housing;
   a sensor extending out of the outlet of the connector housing and into the hub body for sensing status of the catheter hub or for monitoring patient conditions;
   at least one of a smart device and a Cloud server for collecting data sensed by the sensor; and
   a computational core mounted around an exterior of the connector housing, the computational core having a body with a power supply and circuitries mounted to the body.

2. The catheter system of claim 1, wherein the sensor is a first sensor and is mounted in a bore of the outlet of the connector housing.

3. The catheter system of claim 1, further comprising a second sensor, and wherein the second sensor is mounted on the exterior of the hub body.

4. The catheter system of claim 3, wherein the second sensor is mounted to a wing extending from the hub body.

5. The catheter system of claim 2, further comprising a second sensor, and wherein the second sensor is mounted to the catheter tube.

6. The catheter system of claim 1, further comprising a BLE module electrically coupled to the sensor for relaying sensed data to the smart device using BLE connectivity.

7. The catheter system of claim 1, further comprising a BLE module electrically coupled to the sensor and a gateway comprising a BLE module and a Wi-Fi module.

8. The catheter system of claim 7, wherein the sensed data is collected by the Cloud server through the Wi-Fi module of the gateway.

9. The intravenous catheter system of claim 1, wherein the hub body comprises a first hub body section attached to a second hub body section.

10. The catheter system of claim 1, further comprising a fiber optic sensor connecting the sensor to an electronic connector assembly removably connected to the catheter hub.

11. The catheter system of claim 5, wherein sensor mounted to the catheter tube is a fiber optic sensor extending to an electronic connector assembly removably connected to the catheter hub.

12. A catheter system comprising:
    a catheter hub comprising a hub body having an exterior and an interior and an open proximal end;
    a catheter tube having a lumen attached to the catheter hub;
    a sensor mounted to at least one of the hub body and the catheter tube for sensing status of the catheter hub or for monitoring patient conditions;
    a sensor module comprising a connector housing having an inlet and an outlet connected to the hub body of the catheter hub, the sensor module comprising a sensor mounted at least partially in an interior of the connector housing;
    a computational core mounted around an exterior of the connector housing, the computational core having a body with a power supply and circuitries mounted to the body; and
    a protective cover located around an exterior of the computational core.

13. The catheter system of claim 12, wherein the protective cover is made from a pliable material and comprises pockets for accommodating the power supply and the circuitries.

14. The catheter system of claim 12, further comprising a movable piston having a head section, a neck section, and a body section located inside the connector housing and being configured to compress and expand to control flow through the inlet of the connector housing.

15. The catheter system of claim 12, wherein the sensor is connected to a lead and the lead projects from the interior of a connector body to connect to the computational core.

16. The catheter system of claim 12, wherein the inlet of the connector housing is a female luer.

17. The catheter system of claim 1, further comprising a protective cover located around an exterior of the computational core.

18. The catheter system of claim 17, wherein the protective cover is made from a silicone material or a rubber material and comprises one or more pockets for accommodating the power supply and circuitries.

19. The catheter system of claim 1, wherein the inlet of the connector housing is a female luer.

* * * * *